US010465178B2

(12) United States Patent
Ton et al.

(10) Patent No.: US 10,465,178 B2
(45) Date of Patent: *Nov. 5, 2019

(54) PROCESS AND SYSTEM FOR OBTAINING BOTULINUM NEUROTOXIN

(71) Applicant: Allergan, Inc., Irvine, CA (US)

(72) Inventors: Jennifer L. Ton, Irvine, CA (US); Hemant A. Patel, Rancho Santa Margarita, CA (US); Ronald C. Bates, Irvine, CA (US); Wajdie M. Ahmad, Westminster, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,456

(22) Filed: Jul. 31, 2017

(65) Prior Publication Data

US 2017/0327811 A1 Nov. 16, 2017

Related U.S. Application Data

(60) Division of application No. 14/961,327, filed on Dec. 7, 2015, now Pat. No. 9,719,076, which is a division of application No. 14/561,402, filed on Dec. 5, 2014, now Pat. No. 9,206,409, which is a continuation of application No. 13/407,662, filed on Feb. 28, 2012, now Pat. No. 8,932,827, which is a continuation of application No. 13/344,399, filed on Jan. 5, 2012, now Pat. No. 8,927,229, which is a continuation of application No. 12/502,181, filed on Jul. 13, 2009, now Pat. No. 8,129,139.

(51) Int. Cl.
*C12P 1/00* (2006.01)
*C12N 9/52* (2006.01)
*C07K 14/33* (2006.01)
*B01D 15/36* (2006.01)

(52) U.S. Cl.
CPC .............. *C12N 9/52* (2013.01); *B01D 15/361* (2013.01); *B01D 15/362* (2013.01); *B01D 15/363* (2013.01); *C07K 14/33* (2013.01); *C12Y 304/24069* (2013.01)

(58) Field of Classification Search
CPC ........................................................ C12N 9/52
See application file for complete search history.

(56) References Cited

U.S. PATENT DOCUMENTS

| | | | |
|---|---|---|---|
| 4,401,683 A | 8/1983 | Thompson | |
| 5,565,330 A | 10/1996 | Atkinson et al. | |
| 6,558,926 B1 | 5/2003 | Demain et al. | |
| 6,818,409 B2 | 11/2004 | Oguma | |
| 7,148,041 B2 | 12/2006 | Donovan | |
| 7,160,699 B2 | 1/2007 | Wang et al. | |
| 7,189,541 B2 | 3/2007 | Donovan | |
| 7,445,914 B2 | 11/2008 | Donovan | |
| 7,452,697 B2 | 11/2008 | Luo | |
| 7,560,251 B2 | 7/2009 | Wang | |
| 8,129,139 B2 | 3/2012 | Ton et al. | |
| 8,324,349 B2 | 12/2012 | Ton et al. | |
| 8,357,541 B2 | 1/2013 | Ton | |
| 8,409,828 B2 | 4/2013 | Xiang et al. | |
| 8,841,110 B2 | 9/2014 | Xiang et al. | |
| 8,927,229 B2 | 1/2015 | Ton et al. | |
| 8,932,827 B2 | 1/2015 | Ton et al. | |
| 9,206,409 B2 * | 12/2015 | Ton ...................... C07K 14/33 | |
| 2003/0118598 A1 | 5/2003 | Hunt et al. | |
| 2004/0235139 A1 | 11/2004 | Demain et al. | |
| 2005/0238669 A1 * | 10/2005 | Xiang ................... C07K 14/33 424/239.1 |
| 2008/0223103 A1 | 9/2008 | Ping Wang | |
| 2009/0022763 A1 | 1/2009 | Donovan | |
| 2009/0123497 A1 | 5/2009 | Luo | |
| 2009/0124790 A1 | 5/2009 | Luo | |
| 2011/0008843 A1 | 1/2011 | Ton et al. | |

FOREIGN PATENT DOCUMENTS

| | | |
|---|---|---|
| WO | WO 1994/009115 | 1/1993 |
| WO | WO 1996/005222 | 6/1995 |
| WO | WO 1998/054296 | 5/1998 |
| WO | WO 2001/005997 | 7/2000 |
| WO | WO 2001/036655 | 10/2000 |
| WO | WO 2001/058472 | 2/2001 |
| WO | WO 2005/035749 | 8/2004 |
| WO | WO 2005/072433 | 8/2005 |
| WO | WO 2006/096164 | 9/2006 |

OTHER PUBLICATIONS

Bedu-Addo, F., et al. "Use of Biophysical characterization in preformulation development of a heavy-chain fragment of botulinum serotype B: Evaluation of suitable purification process conditions." *Pharmaceutical Research* 21.8 (2004): 1353:1361.

Byrne, M., et al., *Fermentation, Purification, and Efficacy of a Recombinant Vaccine Candidate Against Botulinum Neurotoxin Type F from Pichia pastoris*, Protein Expression and Purification, 2000, 18, pp. 327-337.

Byrne, M., et al. "Purification, potency, and efficacy of the botulinum type A binding domain from Pichia Pastoris as a recombinant vaccine candidate." *Infection and Immunity* 66.10 (1998): 4817-4822.

Chen, F., et al. "Biophysical characterization of the stability of the 150-kilodalton botulinum toxin, the nontoxic component and the 900-kilodalton botulinum toxin complex species." *Infection and Immunity* 66.6 (Jun. 1998): 2420-2425.

(Continued)

*Primary Examiner* — Albert M Navarro
(74) *Attorney, Agent, or Firm* — Laura L. Wine

(57) ABSTRACT

Rapid, animal protein free, chromatographic processes and systems for obtaining high potency, high yield botulinum neurotoxin for research, therapeutic and cosmetic use.

3 Claims, 1 Drawing Sheet

(56) References Cited

OTHER PUBLICATIONS

Coligan, John E., et al., Eds. "Chp. 1:1-88, Strategies of protein purification and characterization." *Current Protocols in Protein Science, Front Matter* Aug. 2003.
Gessler, F., et al. "Production and purification of Clostridium botulinum type C and D neurotoxin." *FEMS Immunology and Medical Microbiology* 24 (1999): 361-367.
Gimenez, J., et al. "Simplified purification method for Clostridium botulinum type E toxin." *Applied and Environmental Microbiology* 53.12 (Dec. 1987): 2827-2830.
Heenan, C.N., et al. *Lehensm.-Wiss. U.-Technol.* 35 (2002): 171-176.
Holdeman, L., et al. "A study of the nutritional requirements and toxin production of clostridium botulinum type F." *Canadian Journal of Microbiology*, 11 (1965): 1009-1019.
Huhtanen, C.N. "Some observations on a perigo-type inhibition of Clostridium botulinum in a simplified medium." *Journal of Milk Food Technology* 38.12 (Dec. 1975): 761-763.
Johnson, E., et al. "Clostridium botulinum and its neurotoxins: a metabolic and cellular perspective." *Toxicon* 39 (2001): 1703-1722.
Johnson, S., et al. "Scale-up of the fermentation and purification of the recombinant heavy chain fragment C of botulinum neurotoxin serotype F, expressed in Pichia Pastoris." *Protein Expression and Purification* 32 (2003): 1-9.
Karasawa, T., et al. "A defined growth medium for clostridium difficle." *Microbiology* 141 (1995): 371-375.
Kohl, A., et al. "Comparison of the effect of botulinum toxin A (BOTOX®) with the highly-purified neurotoxin (NT201) in the extensor digitorum brevis muscle test." *Movement Disorders* 15(Suppl 3) (2000): 165.
Kozaki, H., et al. "Immunological characterization of papain-induced fragments of Clostridium botulinum type A neurotoxin and interaction of the fragments with brain synaptosomes." *Infection and Immunity* 57.9 (1989): 2634-2639.
Li, Y., et al. "Expression and characterization of the heavy chain of tetanus toxin: reconstitution of the fully-recombinant dichain protein in active form." *Journal of Biochemistry* (Tokyo) 125.6 (Jun. 1999): 1200-1208.
Lungdahl, L.G., et al. "Working with anaerobic bacteria." *Manual of Industrial Microbiology and Biotechnology* 1986, Chapter 8: 84-96.
Miwa, Norinaga, et al. *International Journal of Food Microbiology* 49 (1999): 103-106.
Mueller, J.H., et al. "Variable factors influencing the product of tetanus toxin." *Journal of Bacteriology* Mar. 1954, 67.3: 271-277.
Naumann, M., et al. "Botulinum toxin type A in the treatment of focal, axillary and palmar hyperhidrosis and other hyperhidrotic conditions." *European Journal of Neurology* 6(Suppl4) (1999): S111-S115.
Ozutsumi, K., et al. "Rapid, simplified method for production and purification of tetanus toxin." *Applied and Environmental Microbiology* 49.4 (Apr. 1985): 939-943.
Porfirio, Z., et al. "Specific peptides of casein pancreatic digestion enhance the production of tetanus toxin." *Journal of Applied Microbiology* 83 (1997): 678-684.
Prabakaran, S., et al. "Botulinum neurotoxin types B and E: Purification, limited proteolysis by endoproteinase Glu-C and Pepsin, and comparison of their indentified cleaved sites relative to the three-dimensional structure of type A neurotoxin." *Toxicon* 39 (2001): 1515-1531.
Ragona, Rosario Marchese, et al. "Management of Parotid Sialocele with botulinum toxin." *The Laryngoscope* 109 (Aug. 1999): 1344-1346.
Schantz, E.J. et al., J. Jankovic ed. "Preparation and characterization of botulinum toxin type A for human treatment." *Neurological Disease and Therapy. Therapy with Botulinum Toxin* 25 (1994): 41-49.
Schantz, E.J. et al. "Properties and use of botulinum toxin and other microbial neurotoxins in medicine." *Microbiological Reviews* Mar. 1992: 80-99.
Schantz, E.J., et al., Lewis, G.E. "Use of Chrystalline type A botulinum toxin in medical research." *Biomedical Aspects of Botulism*, Academic Press, Inc., George E. Lewis, Jr., Ed., 1981: 143-150.
Schiefer-Ullrich, H., et al. "Comparative studies on physiology and taxonomy of obligatory purinolytic clostridia." *Archives of Microbiology* 138 (1984): 345-353.
Siegel, L.S. "Fermentation kinetics of botulinum toxin production (types A, B and E)." Biomedical aspects of botulism, New York: Academic Press 1981: 121-128.
Siegel, L.S. "Toxin production by Clostridium botulinum type A under various fermentation conditions." *Applied and Environmental Microbiology* Oct. 1979: 606-611.
Simpson, L. S. "Isolation and Characterization of the Botulinum Neurotoxins", Methods in Enzymology, Preparation of Toxins, vol. 165; (1988): 76-85.
Tse, et al. *European Journal of Ciochemistry* 122 (1982): 493-500.
Weatherly, G., et al. "Initial purification of recombinant botulinum neurotoxin fragments for pharmaceutical production using hydrophobic charge induction chromatography." *Journal of Chromatography A* 952 (2002): 99-110.
Whitmer, M.E. et al. "Development of improved defined media for clostridium botulinum serotypes A, B and E." *Applied and Environmental Microbiology* 54.3 (Mar. 1988): 753-759.
Young-Perkins, et al. *Journal of Food Science* 52 (1987): 1084-1088.

* cited by examiner

PROCESS AND SYSTEM FOR OBTAINING BOTULINUM NEUROTOXIN

CROSS REFERENCE TO RELATED APPLICATIONS

This application is a divisional of Ser. No. 14/961,327, filed Dec. 7, 2015, now U.S. Pat. No. 9,719,076, which is a divisional of application Ser. No. 14/561,402, filed Dec. 5, 2014, now U.S. Pat. No. 9,206,409, which is a continuation of application Ser. No. 13/407,662, filed Feb. 28, 2012, now U.S. Pat. No. 8,932,827, which is a continuation of application Ser. No. 13/344,399, filed Jan. 5, 2012, now U.S. Pat. No. 8,927,229, which is a continuation of application Ser. No. 12/502,181, filed Jul. 13, 2009, now U.S. Pat. No. 8,129,139. The entire contents of each are herein incorporated by reference in their entireties.

BACKGROUND

The present invention relates to systems and processes for obtaining a Clostridial neurotoxin, methods for making a pharmaceutical composition therefrom and to therapeutic and cosmetic uses of the pharmaceutical composition so made. In particular, the present invention relates to a rapid, animal protein free, chromatographic process and system for obtaining a high potency, high purity, and high yield biologically active botulinum neurotoxin.

A pharmaceutical composition suitable for administration to a human or animal for a therapeutic, diagnostic, research or cosmetic purpose comprises an active ingredient and one or more excipients, buffers, carriers, stabilizers, tonicity adjusters, preservatives and/or bulking agents. The active ingredient in a pharmaceutical composition can be a biologic such as a botulinum neurotoxin. Known methods (such as the Schantz method) for obtaining a botulinum neurotoxin useful as the active ingredient in a pharmaceutical composition are multi-week culturing, fermentation and purification processes which use animal-derived proteins, such as meat broth and casein used in culture and fermentation media, and animal derived purification enzymes. Administration to a patient of a pharmaceutical composition made through use of animal derived products can entail risk of administering pathogens or an infectious agent, such as a prion. Additionally, known animal protein free methods for obtaining a botulinum toxin are also time-consuming processes (i.e. take more than a week to complete) with numerous upstream (culturing and fermentation) and downstream (purification) steps, and yet still result in obtaining a botulinum neurotoxin with detectable impurities.

Botulinum Toxin

The genus *Clostridium* has more than one hundred and twenty seven species, grouped by morphology and function. The anaerobic, gram positive bacterium *Clostridium botulinum* produces a potent polypeptide neurotoxin, botulinum toxin (synonymously "toxin"), which causes a neuroparalytic illness in humans and animals known as botulism. Symptoms of botulinum toxin intoxication can progress from difficulty walking, swallowing, and speaking to paralysis of the respiratory muscles and death.

One unit of botulinum toxin is defined as the $LD_{50}$ upon intraperitoneal injection into female Swiss Webster mice weighing about 18-20 grams each. One unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. The botulinum toxins apparently bind with high affinity to cholinergic motor neurons and translocate into the neuron and block the presynaptic release of acetylcholine.

Botulinum toxins have been used in clinical settings for the treatment of e.g. neuromuscular disorders characterized by hyperactive skeletal muscles. Botulinum toxin type A has been approved by the U.S. Food and Drug Administration (FDA) for the treatment of essential blepharospasm, strabismus and hemifacial spasm in patients over the age of twelve, cervical dystonia, glabellar line (facial) wrinkles and for treating hyperhidrosis. The FDA has also approved a botulinum toxin type B for the treatment of cervical dystonia.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin type A is a zinc endopeptidase which can specifically hydrolyze a peptide linkage of the intracellular, vesicle-associated protein (VAMP, also called synaptobrevin) 25 kiloDalton (kDa) synaptosomal associated protein (SNAP-25). Botulinum type E also cleaves SNAP-25 but targets different amino acid sequences within this protein, as compared to botulinum toxin type A. Botulinum toxin types B, D, F and G act on VAMP with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the active botulinum toxin protein molecule (also known as "pure toxin" or as the "neurotoxic component") from a botulinum toxin complex, for all seven of the known botulinum toxin serotypes, is about 150 kDa. Interestingly, the botulinum toxins are released by Clostridial bacterium as complexes comprising the 150 kDa neurotoxic component along with one or more associated non-toxin proteins. Thus, the botulinum toxin type A complex can be produced by Clostridial bacterium as 900 kDa, 500 kDa and 300 kDa forms (approximate molecular weights). Botulinum toxin types B and $C_1$ are apparently produced as only a 500 kDa complex. Botulinum toxin type D is produced as both 300 kDa and 500 kDa complexes. Finally, botulinum toxin types E and F are produced as only approximately 300 kDa complexes. The complexes (i.e. molecular weight greater than about 150 kDa) contain hemagglutinin (HA) proteins and a non-toxin non-hemagglutinin (NTNH) protein. Thus, a botulinum toxin complex can comprise a botulinum toxin molecule (the neurotoxic component) and one or more HA proteins and/or NTNH protein. These two types of non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kDa molecular weight) botulinum toxin complexes may result in a slower rate of diffusion of the botulinum toxin away from a site of intramuscular injection of a botulinum toxin complex. The success of botulinum toxin type A to treat a variety of clinical conditions has led to interest in other botulinum toxin serotypes. Thus, at least botulinum toxins types, A, B, E and F have been used clinically in humans. Additionally, a formulation of the neurotoxic component (i.e. without the associated non-toxin proteins) is sold in Europe under the tradename XEOMIN (Merz Pharmaceuticals, Frankfurt, Germany).

The botulinum toxin type A is known to be soluble in dilute aqueous solutions at pH 4-6.8. At pH above about 7 the stabilizing non-toxin proteins dissociate from the neurotoxin, resulting in a gradual loss of toxicity, particularly as the pH and temperature rise (Schantz E. J., et al *Preparation and characterization of botulinum toxin type A for human treatment* (in particular pages 44-45), being chapter 3 of Jankovic, J., et al, Therapy with Botulinum Toxin, Marcel Dekker, Inc, 1994).

As with enzymes generally, the biological activities of the botulinum toxins (which are intracellular peptidases) are dependant, at least in part, upon their three dimensional conformation. Dilution of the toxin from milligram quantities to a solution containing nanograms per milliliter presents significant difficulties, such as, for example, tendency for toxin to adhere to surfaces and thus reduce the amount of available toxin. Since the toxin may be used months or years after the toxin containing pharmaceutical composition is formulated, the toxin is stabilized with a stabilizing agent such as albumin, sucrose, trehalose and/or gelatin.

A commercially available botulinum toxin containing pharmaceutical composition is sold under the trademark BOTOX® (botulinum toxin type A purified neurotoxin complex) available commercially from Allergan, Inc., of Irvine, Calif. Each 100 unit vial of BOTOX® consists of about 5 ng of purified botulinum toxin type A complex, 0.5 mg human serum albumin, and 0.9 mg sodium chloride, vacuum-dried form and intended for reconstitution with sterile normal saline without a preservative (0.9% sodium chloride injection). Other commercially available, botulinum toxin-containing pharmaceutical compositions include Dysport® (*Clostridium botulinum* type A toxin hemagglutinin complex with human serum albumin and lactose in the botulinum toxin pharmaceutical composition), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Solstice Neurosciences of San Diego, Calif. The neurotoxic component (the 150 kDa toxin molecule) and botulinum toxin complexes (300 kDa to 900 kDa) can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo.

Animal protein free and/or chromatographic methods for obtaining a botulinum neurotoxin are disclosed in U.S. Pat. Nos. 7,445,914; 7,452,697; 7,354,740; 7,160,699; 7,148, 041, and; 7,189,541. Also of interest are U.S. patent application Ser. No. 11/609,449 entitled "Media for *Clostridium* Bacterium", filed Dec. 12, 2006; Ser. No. 12/098,896 entitled "Animal Product Free Media and Processes for Obtaining a Botulinum Toxin", filed Apr. 7, 2008; Ser. No. 11/932,689 entitled "Chromatographic Method and System for Purifying a Botulinum Toxin", filed Oct. 31, 2007; Ser. No. 11/932,789 entitled "Chromatographic Method and System for Purifying a Botulinum Toxin" filed Oct. 31, 2007, and; Ser. No. 12/234,537, entitled "Animal Product Free Media And Processes For Obtaining A Botulinum Toxin", filed Sep. 19, 2008.

Botulinum toxin for use in a pharmaceutical composition can be obtained by anaerobic fermentation of *Clostridium botulinum* using the well known Schantz process (see e.g. Schantz E. J., et al., *Properties and use of botulinum toxin and other microbial neurotoxins in medicine*, Microbiol Rev 1992 March; 56(1):80-99; Schantz E. J., et al., *Preparation and characterization of botulinum toxin type A for human treatment*, chapter 3 in Jankovic J, ed. Neurological Disease and Therapy. Therapy with botulinum toxin (1994), New York, Marcel Dekker; 1994, pages 41-49, and; Schantz E. J., et al., *Use of crystalline type A botulinum toxin in medical research*, in: Lewis G E Jr, ed. Biomedical Aspects of Botulism (1981) New York, Academic Press, pages 143-50). The Schantz process for obtaining a botulinum toxin makes use of animal products for example as reagents and as part of the culture and fermentation media.

A number of steps are required to make a Clostridial toxin pharmaceutical composition suitable for administration to a human or animal for a therapeutic, diagnostic, research or cosmetic purpose. These steps can include obtaining a purified Clostridial toxin and then compounding the purified Clostridial toxin. A first step can be to plate and grow colonies of Clostridial bacteria, typically on blood agar plates, in an environment conducive to anaerobic bacterial growth, such as in a warm anaerobic atmosphere. This step allows Clostridial colonies with desirable morphology and other characteristics to be obtained. In a second step selected Clostridial colonies can be fermented in a first suitable medium and if additionally desired, into a second fermentation medium. After a certain period of fermentation, the Clostridial bacteria typically lyse and release Clostridial toxin into the medium. Thirdly, the medium can be purified so as to obtain a bulk toxin. Typically medium purification to obtain bulk toxin is carried out using, among other reagents, animal-derived enzymes, such as DNase and RNase, which are used to degrade and facilitate removal of nucleic acids. The resulting bulk toxin can be a highly purified toxin with a particular specific activity. After stabilization in a suitable buffer, the bulk toxin can be compounded with one or more excipients to make a Clostridial toxin pharmaceutical composition suitable for administration to a human. The Clostridial toxin pharmaceutical composition can comprise a Clostridial toxin as an active pharmaceutical ingredient (API). The pharmaceutical composition can also include one or more excipients, buffers, carriers, stabilizers, preservatives and/or bulking agents.

The *Clostridium* toxin fermentation step can result in a fermentation medium solution that contains whole *Clostridium* bacteria, lysed bacteria, culture medium nutrients and fermentation by-products. Filtration of this culture solution so as to remove gross elements, such as whole and lysed bacteria, provides a harvest/clarified medium. The clarified medium comprises a Clostridial toxin and various impurities and is processed to obtain a concentrated Clostridial toxin, which is called bulk toxin.

Fermentation and purification processes for obtaining a bulk Clostridial toxin using one or more animal derived products (such as the milk digest casein, DNase and RNase) are known. An example of such a known non-animal product free ("NAPF") process for obtaining a botulinum toxin complex is the Schantz process and modifications thereto. The Schantz process (from initial plating, cell culture through to fermentation and toxin purification) makes use of a number of products derived from animal sources such as, for example, animal derived Bacto Cooked Meat medium in the culture vial, Columbia Blood Agar plates for colony growth and selection, and casein in the fermentation media. Additionally, the Schantz bulk toxin purification process makes use of DNase and RNase from bovine sources to hydrolyze nucleic acids present in the toxin containing fermentation medium. Concerns have been expressed regarding a potential for a viral and transmissible spongiform encephalopathy (TSE), such as a bovine spongiform encephalopathy (BSE), contamination when animal products are used in a process for obtaining an API and/or in a process for making (compounding) a pharmaceutical composition using such an API.

A fermentation process for obtaining a tetanus toxoid that uses reduced amounts of animal-derived products (referred to as animal product free or "APF" fermentation processes; APF encompasses animal protein free) is known, see e.g. U.S. Pat. No. 6,558,926. An APF fermentation process for obtaining a Clostridial toxin, has the potential advantage of reducing the (the already very low) possibility of contamination of the ensuing bulk toxin with viruses, prions or other undesirable elements which can then accompany the active pharmaceutical ingredient, Clostridial toxin, as it is compounded into a pharmaceutical composition for administration to humans.

Chromatography, such as column chromatography for example, can be used to separate a particular protein (such as a botulinum neurotoxin) from a mixture of proteins, nucleic acids, cell debris, etc. in a process known as fractionation or purification. The protein mixture typically passes through a glass or plastic column containing, for example, a solid, often porous media (often referred to as beads or resin). Different proteins and other compounds pass through the matrix at different rates based on their specific chemical characteristics and the way in which these characteristics cause them to interact with the particular chromatographic media utilized.

The choice of media determines the type of chemical characteristic by which the fractionation of the proteins is based. There are four basic types of column chromatography; ion-exchange, gel filtration, affinity and hydrophobic interaction. Ion-exchange chromatography accomplishes fractionation based on surface electrostatic charge using a column packed with small beads carrying either a positive or a negative charge. In gel filtration chromatography, proteins are fractionated based on their size. In affinity chromatography, proteins are separated based on their ability to bind to specific chemical groups (ligand) attached to beads in the column matrix. Ligands can be biologically specific for a target protein. Hydrophobic interaction chromatography accomplishes fractionation based on surface hydrophobicity.

Column chromatography to purify (fractionate) a Clostridial toxin is well known. See for example the following publications:

1. Ozutsumi K., et al, *Rapid, simplified method for production and purification of tetanus toxin*, App & Environ Micro, April 1985, p 939-943, vol 49, no. 4. (1985) discloses use of high pressure liquid chromatography (HPLC) gel filtration to purify tetanus toxin.
2. Schmidt J. J., et al., *Purification of type E botulinum neurotoxin by high-performance ion exchange chromatography*, Anal Biochem 1986 July; 156(1):213-219 discloses use of size exclusion chromatography or ion exchange chromatograph to purify botulinum toxin type E. Also disclosed is use of protamine sulfate instead of ribonuclease (RNase).
3. Simpson L. L., et al., *Isolation and characterization of the botulinum neurotoxins* Simpson L L; Schmidt J J; Middlebrook J L, In: Harsman S, ed. Methods in Enzymology. Vol. 165, Microbial Toxins: Tools in Enzymology San Diego, Calif.: Academic Press; vol 165:pages 76-85 (1988) discloses purification of botulinum neurotoxins using gravity flow chromatography, HPLC, capture steps using an affinity resin, size exclusion chromatography, and ion (anion and cation) exchange chromatography, including use of two different ion exchange columns. Various Sephadex, Sephacel, Trisacryl, S and Q columns are disclosed.
4. Zhou L., et al., *Expression and purification of the light chain of botulinum neurotoxin A: A single mutation abolishes its cleavage of SNAP-25 and neurotoxicity after reconstitution with the heavy chain*, Biochemistry 1995; 34(46):15175-81 (1995) discloses use of an amylose affinity column to purify botulinum neurotoxin light chain fusion proteins.
5. Kannan K., et al., *Methods development for the biochemical assessment of Neurobloc (botulinum toxin type B)*, Mov Disord 2000; 15(Suppl 2):20 (2000) discloses use of size exclusion chromatography to assay a botulinum toxin type B.
6. Wang Y-c, *The preparation and quality of botulinum toxin type A for injection (BTXA) and its clinical use*, Dermatol Las Faci Cosm Surg 2002; 58 (2002) discloses ion exchange chromatography to purify a botulinum toxin type A. This reference discloses a combination of precipitation and chromatography techniques.
7. Johnson S. K., et al., *Scale-up of the fermentation and purification of the recombination heavy chain fragment C of botulinum neurotoxin serotype F, expressed in Pichia pastoris*, Protein Expr and Purif 2003; 32:1-9 (2003) discloses use of ion exchange and hydrophobic interaction columns to purify a recombinant heavy chain fragment of a botulinum toxin type F.
8. Published U.S. patent application 2003/0008367 A1 (Oguma) discloses use of ion exchange and lactose columns to purify a botulinum toxin.

The purification methods summarized above relate to small-scale purification of the neurotoxic component of a botulinum toxin complex (i.e. the approximately 150 kDa neurotoxic molecule), or a specific component of the neurotoxic component, as opposed to purification of the entire 900 kDa botulinum toxin complex.

Furthermore, existing processes, including commercial scale processes, for obtaining a botulinum toxin suitable for compounding into a botulinum toxin pharmaceutical composition typically include a series of precipitation steps to separate the toxin complex from impurities that accompany the botulinum toxin from the fermentation process. Notably, precipitation techniques are widely used in the biopharmaceutical industry to purification a botulinum toxin. For example, cold alcohol fractionation (Cohn's method) or precipitation is used to remove plasma proteins. Unfortunately, previous precipitation techniques for purifying a botulinum toxin have the drawbacks of low resolution, low productivity, difficulty of operation, difficulty to control and/or validate and/or difficulty to scale-up or scale-down. Previously published U.S. patent application Ser. No. 11/452,570, published Oct. 12, 2006, discloses steps such as centrifugation, acid precipitation, ethanol precipitation, acidification steps, and ammonium sulfate precipitation utilized in various animal-protein free and NAPF processes (for a detailed discussion, see U.S. Published Patent App. No. 2006/0228780, herein incorporated by reference in its entirety). Some distinctions between a non-animal protein free process and an animal protein free processes for obtaining a botulinum neurotoxin are shown therein.

What are needed therefore are rapid, relatively smaller scale yet high yield systems and processes for obtaining high purity, highly potent botulinum neurotoxin, which can be used for research purposes and/or to make a pharmaceutical composition.

SUMMARY

The present invention meets this need and provides high purity, highly potent botulinum neurotoxins obtainable by rapid, smaller scaled, commercially useful, high yield, animal protein free, chromatographic systems and processes. The resultant botulinum neurotoxin is useful for making a pharmaceutical composition. The Clostridial toxin obtained by the practice of our invention is preferably a botulinum neurotoxin and most preferably a botulinum neurotoxin type A complex of about 900 kDa or the 150 kDa neurotoxic component therefrom. Our invention does not require NAPF reagents, such as DNase and RNase.

Definitions

The following words and terms used herein have the following definitions.

"About" means that the item, parameter or term so qualified encompasses a range of plus or minus ten percent above and below the value of the stated item, parameter or term.

"Administration," or "to administer" means the step of giving (i.e. administering) a pharmaceutical composition or active ingredient to a subject. The pharmaceutical compositions disclosed herein are "locally administered" by e.g. intramuscular (i.m.), intradermal, subcutaneous administration, intrathecal administration, intracranial, intraperitoneal (i.p.) administration, topical (transdermal) and implantation (i.e. of a slow-release device such as polymeric implant or miniosmotic pump) routes of administration.

"Animal product free" or "substantially animal product free" encompasses, respectively, "animal protein free" or "substantially animal protein free" and means the absence or substantial absence of blood derived, blood pooled and other animal derived products or compounds. "Animal" means a mammal (such as a human), bird, reptile, fish, insect, spider or other animal species. "Animal" excludes microorganisms, such as bacteria. Thus, an APF medium or process or a substantially APF medium or process within the scope of the present invention can include a botulinum toxin or a Clostridial botulinum bacterium. For example, an APF process or a substantially APF process means a process which is either substantially free or essentially free or entirely free of animal-derived proteins, such as immunoglobulins, meat digest, meat by products and milk or dairy products or digests.

"Botulinum toxin" or "botulinum neurotoxin: means a neurotoxin produced by *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F and G. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention. "Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 90%, preferably more than 95%, and most preferably more than 99% of the non-botulinum toxin proteins and impurities removed. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum, Clostridium butyricum* or *Clostridium baratti*, as well as a Clostridial neurotoxin made recombinantly by a non-Clostridial species.

"Entirely free" ("consisting of" terminology) means that within the detection range of the instrument or process being used, the substance cannot be detected or its presence cannot be confirmed.

"Essentially free" (or "consisting essentially of") means that only trace amounts of the substance can be detected.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Pharmaceutical composition" means a formulation in which an active ingredient can be a botulinum toxin. The word "formulation" means that there is at least one additional ingredient (such as, for example and not limited to, an albumin [such as a human serum albumin or a recombinant human albumin] and/or sodium chloride) in the pharmaceutical composition in addition to a botulinum neurotoxin active ingredient. A pharmaceutical composition is therefore a formulation which is suitable for diagnostic, therapeutic or cosmetic administration (e.g. by intramuscular or subcutaneous injection or by insertion of a depot or implant) to a subject, such as a human patient. The pharmaceutical composition can be: in a lyophilized or vacuum dried condition, a solution formed after reconstitution of the lyophilized or vacuum dried pharmaceutical composition with saline or water, for example, or; as a solution that does not require reconstitution. The active ingredient can be one of the botulinum toxin serotypes A, B, $C_1$, D, E, F or G or a botulinum toxin, all of which can be made natively by Clostridial bacteria. As stated, a pharmaceutical composition can be liquid or solid, for example vacuum-dried. Exemplary methods for formulating a botulinum toxin active ingredient pharmaceutical composition are disclosed in published U.S. patent publication 2003/0118598, filed Nov. 5, 2002, herein incorporated by reference in its entirety.

"Substantially free" means present at a level of less than one percent by weight of a culture medium, fermentation medium, pharmaceutical composition or other material in which the weight percent of a substance (such as an animal product, animal protein or animal derived product or protein) is assessed.

"Therapeutic formulation" means a formulation can be used to treat and thereby alleviate a disorder or a disease and/or symptom associated thereof, such as a disorder or a disease characterized by hyperactivity (e.g. spasticity) of a peripheral muscle or gland, (e.g. sweat gland).

"Therapeutically effective amount" means the level, amount or concentration of an agent (e.g. such as a botulinum toxin or pharmaceutical composition comprising botulinum toxin) needed to treat a disease, disorder or condition without causing significant negative or adverse side effects.

"Treat", "treating", or "treatment" means an alleviation or a reduction (which includes some reduction, a significant reduction a near total reduction, and a total reduction), resolution or prevention (temporarily or permanently) of an disease, disorder or condition, such as a buttock deformity, so as to achieve a desired therapeutic or cosmetic result, such as by healing of injured or damaged tissue, or by altering, changing, enhancing, improving, ameliorating and/or beautifying an existing or perceived disease, disorder or condition. A treatment effect, such as an alleviating effect from administration of a botulinum neurotoxin may not appear clinically for between 1 to 7 days after administration of the botulinum neurotoxin to a patient for example and can have a duration of effect of from about 1 month to about 1 year or any range of time therebetween, for example, depending upon the condition and particular case being treated.

Percentages are based on weight per volume unless otherwise noted.

APF means animal product/protein free

CV means column volume

DF means diafiltration

ELISA means enzyme-linked immunosorbent assay.

IAPF, as in "IAPF system" or "IAPF process", means "improved animal protein free" system or process. An IAPF system or process includes the use of either two chromatography media or three chromatography media to purify a botulinum toxin or neurotoxin component, as specifically detailed herein. Chromatography media includes chromatography resins, as known in the art. Batches of botulinum neurotoxin obtained by use of two chromatography media are herein designated as IAPF.

FAPF, as in "FAPF system" or "FAPF process", means "further improved animal protein free" system or process. Accordingly, FAPF is an IAPF process, and a FAPF system or process means that three chromatography media are used to purify a botulinum toxin or neurotoxin component. Batches of botulinum neurotoxin obtained by use of three chromatography media are herein designated as FAPF.

NAPF means non-animal protein free

SDS-PAGE means sodium dodecylsulfate polyacrylamide gel electrophoresis

SEC-HPLC means size exclusion high performance liquid chromatography

UF means ultrafiltration.

In one embodiment of the invention, a substantially APF chromatographic process for obtaining a biologically active botulinum neurotoxin is provided, the process comprising the following steps of (a) providing a substantially APF fermentation medium; (b) fermenting *Clostridium botulinum* bacteria in the fermentation medium, and; (c) recovering the biologically active botulinum neurotoxin from the fermentation medium by contacting the fermentation medium with an anion exchange chromatography media followed by contacting an eluent from the anion exchange chromatography medium with a cation exchange chromatography media, to thereby obtain the biologically active botulinum neurotoxin from the substantially APF chromatographic process. In particular embodiments, the process can provide a botulinum neurotoxin that comprises less than one part per million (ppm) residual nucleic acid which is one nanogram or less of residual nucleic acid for each milligram of the botulinum neurotoxin obtained. In still another aspect, the process is carried out in one week or less.

In one example, media having a ratio of 3:1:1 means a botulinum toxin culture/fermentation medium containing 3% HySoy, 1% HyYeast, and 1% glucose. HySoy (Quest product no. 5X59022) is a source of peptides made by enzymatic hydrolysis of soy. HyYeast (HyYeast, Quest product no. 5Z10102 or 5Z10313 is a baker's yeast extract. In another example, media having a ratio of 5:1:1 means a botulinum toxin culture/fermentation medium containing 5% HySoy, 1% HyYeast, and 1% glucose.

Another embodiment provides a substantially APF chromatographic process for obtaining a biologically active botulinum neurotoxin type A complex, the process comprising the following sequential steps of culturing *Clostridium botulinum* bacteria in a substantially APF culture medium; fermenting *Clostridium botulinum* bacteria from the culture medium in about 2 L to about 75 L of a substantially APF fermentation medium, more preferably in about 2 L to about 50 L of a substantially APF fermentation medium, even more preferably in about 2 L to about 30 L of a substantially APF fermentation medium (particular embodiments have at least one of the culture medium and the fermentation medium including a vegetable protein and/or a vegetable protein derivative, for example a hydrolyzed vegetable protein), harvesting the fermentation medium by removing cellular debris present in the fermentation medium using filtration or centrifugation; concentrating the harvested fermentation medium by filtration, such as by ultrafiltration (UF) for example; diluting the concentrated fermentation medium by adding a buffer. Following dilution with the buffer, a first contacting step is undertaken in which the diluted harvested fermentation medium is contacted with an anion exchange media so that the biologically active botulinum neurotoxin becomes captured by the anion exchange media; followed by elution of the captured botulinum neurotoxin from the anion exchange media to thereby obtain a first eluent containing the botulinum toxin; performing a second contacting step in which the first eluent is contacted with a cation exchange media to remove impurities from the first eluent, to thereby obtain a second eluent containing the botulinum toxin; followed by processing the second eluent by diafiltration (DF); and filtering the processed second eluent, thereby obtaining biologically active botulinum neurotoxin type A complex using a substantially APF chromatographic process. The botulinum neurotoxin type A complex obtained can have a potency of about $2.0 \times 10^7$ units/mg to about $6.0 \times 10^7$ units/mg of botulinum neurotoxin type A complex. In particular examples botulinum neurotoxin type A complex having a potency of between about $2.4 \times 10^7$ units/mg to about $5.9 \times 10^7$ units/mg, for example, can be obtained.

In a particular embodiment, the process utilizes fermentation medium comprising no more than about 5% w/v of a vegetable-derived protein product, no more than about 2% w/v of a yeast extract and no more than about 2% w/v glucose, and wherein the pH level of the fermentation medium is from about 6.5 to about pH 8.0, more preferably from about pH 6.8 to about pH 7.6, at the commencement of the fermenting step. In a particular embodiment, the culturing step is carried out until the optical density of the culture medium at about 540 nanometers (nm) is between about 0.8 absorbance units (AU) and about 4.5 AU. The culturing step is preferably initiated by introducing a *Clostridium botulinum* APF working cell bank content to the culture medium, where the working cell bank content comprises at least about $1 \times 10^4$ colony-forming units, preferably from about $1 \times 10^4$ to about $5 \times 10^7$ colony-forming units of *Clostridium botulinum* per milliliter of the working cell bank, and where the *Clostridium botulinum* bacterium in the working cell bank have a substantially uniform morphology. In still yet another embodiment, the fermenting step is carried out for about 60 to 80 hours and until an optical density of the fermentation medium at about 890 nm decreases to between about 0.05 AU to about 0.7 AU. In one aspect, the botulinum neurotoxin obtained by a substantially APF chromatographic process comprises less than 1 ppm of residual nucleic acid and the process is carried out in one week or less.

In yet another embodiment, an APF process utilizing chromatography for obtaining a biologically active botulinum neurotoxin is provided, comprising the sequential steps of: (a) adding *Clostridium botulinum* bacteria from an APF working cell bank to an APF culture medium; (b) culturing the *Clostridium botulinum* bacteria in the culture medium; (c) fermenting the *Clostridium botulinum* bacteria from step (b) in an APF fermentation medium until *Clostridium botulinum* cell lysis occurs; (d) harvesting the fermentation culture to provide a harvested fermentation medium; (e) subjecting the harvested fermentation medium to concentration by filtration; (f) diluting the filtered fermentation medium by addition of a buffer to obtain a diluted fermentation medium; (g) a first contacting step in which the diluted fermentation medium is contacted with a capture chromatography media, wherein the capture chromatography media is an anion exchange media; (h) a second contacting step wherein an eluent from the first contacting step is contacted with a polishing chromatography media, wherein the polishing chromatography media is a cation exchange media, and (i) filtering eluent from the second contacting step, thereby obtaining biologically active botulinum neurotoxin by the improved APF process, wherein the botulinum neurotoxin obtained comprises 1 ppm of residual nucleic acid or less than 1 ppm of residual nucleic acid and the process is carried out in one week or less.

In one aspect, a substantially animal product free (APF) chromatographic system for obtaining a biologically active botulinum neurotoxin is provided, comprising a substantially APF fermentation medium, *Clostridium botulinum* bacteria for fermenting in the fermentation medium, an anion exchange chromatography medium for recovering biologically active botulinum neurotoxin from the fermentation medium, and a cation exchange chromatography medium for recovering further biologically active botulinum neurotoxin from an eluent from the anion exchange chromatography medium, thereby obtaining biologically active botulinum neurotoxin from a substantially APF chromatography process. In particular configurations, the system can further comprise a first apparatus for anaerobically culturing the *Clostridium botulinum* bacteria in a substantially APF culture medium, and can further be comprised of a second apparatus for anaerobically fermenting the *Clostridium botulinum* bacteria in the substantially APF fermentation medium, wherein the *Clostridium botulinum* bacteria are obtained from the first apparatus. For clarification, the system can include a harvesting apparatus for removing cellular debris from the fermentation medium obtained from the second apparatus, to thereby provide a harvested fermentation medium. The harvested fermentation medium can be passed through a concentration and diluting apparatus to concentrate then subsequently dilute the harvested fermentation medium.

In a particular example, the system can also include hydrophobic interaction medium for recovering further purified biologically active botulinum neurotoxin from an eluent from the cation exchange chromatography medium. Additionally, a filtration apparatus for reducing bioburden in the obtained biologically active botulinum neurotoxin can also make up the system, for reducing the bioburden of the biologically active botulinum neurotoxin obtained by utilizing either two or three chromatography medium. In a specific example, an anaerobic chamber having an integrated high efficiency particulate air filter within its workspace, for culturing *Clostridium botulinum* bacteria in the substantially APF culture medium, can be utilized. Exemplary systems can provide botulinum neurotoxin having a potency of at least about $2.0 \times 10^7$ units/mg of botulinum neurotoxin and the botulinum neurotoxin obtained comprises one ng or less than one ng of residual nucleic acid for each mg of the botulinum neurotoxin obtained. In particular embodiments, the substantially APF fermentation medium is provided in an amount of from about 2 L to about 75 L; and from about 200 mL to about 1 L of substantially APF culture medium is utilized.

In another aspect of our invention, a substantially APF system using chromatography for obtaining a biologically active botulinum neurotoxin is provided, the system comprising a first apparatus for culturing *Clostridium botulinum* bacteria, the first apparatus capable of containing a substantially APF culture medium; a second apparatus for fermenting *Clostridium botulinum* bacteria which have been cultured in the first apparatus, the second apparatus capable of containing a substantially APF fermentation medium; a third apparatus for harvesting the fermentation medium; a fourth apparatus for concentrating the harvested fermentation medium and diluting the filtered fermentation medium; a fifth apparatus for carrying out a first purification of the botulinum neurotoxin from the harvested medium, wherein the fifth apparatus comprises an anion exchange chromatography media, thereby obtaining a first purified botulinum neurotoxin; and a sixth apparatus for carrying out a second purification of the botulinum neurotoxin wherein the sixth apparatus comprises a cation exchange chromatography media, to thereby obtain a second purified botulinum neurotoxin, wherein the botulinum neurotoxin obtained has a potency of at least about $2.0 \times 10^7$ units/mg of botulinum neurotoxin to about $5.9 \times 10^7$ units/mg of botulinum neurotoxin, the botulinum neurotoxin obtained comprises one ng or less than one ng of residual nucleic acid for each mg of the botulinum neurotoxin obtained and the process is carried out in one week or less. In particular embodiments, the botulinum neurotoxin obtained can have a potency of at least $4.4 \times 10^7$ units/mg of botulinum neurotoxin. In a particular embodiment of the system, the system can further comprise a seventh apparatus for carrying out a further purification of the botulinum neurotoxin obtained from the sixth apparatus, wherein the seventh apparatus comprises a hydrophobic interaction media, thereby obtaining a third purified botulinum neurotoxin. In an additional embodiment, the system can further comprise an eighth apparatus comprising a membrane for filtering eluent from the seventh apparatus.

Another aspect of our invention includes a substantially APF chromatographic system for obtaining a biologically active botulinum neurotoxin comprising a first apparatus for anaerobic culturing *Clostridium botulinum* bacteria, the first apparatus capable of containing from about 200 mL to about 1 L of a substantially APF culture medium; a second apparatus comprising an anaerobic chamber having an integrated high efficiency particulate air filter within the chamber capable of containing the first apparatus; a third apparatus for anaerobic fermentation of Clostridium botulinum bacteria which has been cultured in the first apparatus, the third apparatus capable of containing from about 2 L to about 75 L of a substantially APF fermentation medium, preferably from about 2 L to about 30 L of a substantially APF fermentation medium and including at least one disposable probe selected from the group consisting of a reduction-oxidation probe, a pH probe and a turbidity probe; a fourth apparatus for harvesting the fermentation medium; a fifth apparatus for concentrating the harvested fermentation medium and diluting the filtered fermentation medium; a sixth apparatus for carrying out a first purification of botulinum neurotoxin obtained from the harvested fermentation medium, the sixth apparatus comprising an anion exchange chromatography media, thereby obtaining a first purified botulinum neurotoxin; a seventh apparatus for carrying out a second purification of the botulinum neurotoxin the seventh apparatus comprising a cation exchange chromatography media, thereby obtaining a second purified botulinum neurotoxin; an eighth apparatus for carrying out a third purification of the second purified botulinum neurotoxin, the eighth apparatus comprising hydrophobic interaction media to thereby obtain a third purified botulinum neurotoxin; and a ninth apparatus for filtering the third purified botulinum neurotoxin, the ninth apparatus comprising a filtration membrane, wherein the botulinum neurotoxin obtained has a potency of about $2.4 \times 10^7$ units/mg of botulinum neurotoxin to about $5.9 \times 10^7$ units/mg of botulinum neurotoxin, the botulinum neurotoxin obtained comprises one ng or less than one ng of residual nucleic acid for each mg of the botulinum neurotoxin obtained and the process is carried out in one week or less. In accordance with these processes, a biologically active botulinum neurotoxin is thereby obtained, and in particular examples, the botulinum neurotoxin obtained has a potency of at least about $4.4 \times 10^7$ units/mg of botulinum neurotoxin.

In accordance with processes and systems herein disclosed, biologically active botulinum neurotoxin is thereby obtained. In particular embodiments, the biologically active botulinum neurotoxin obtained by the process and systems herein disclosed has a molecular weight of about 900 kDa.

Our invention further includes a method for making a substantially APF pharmaceutical composition in which the active ingredient is a biologically active botulinum neurotoxin, the method comprising the steps of: (a) obtaining a biologically active botulinum neurotoxin by: (i) providing a fermentation medium which is substantially free of an animal product; (ii) fermenting Clostridium botulinum bacteria in the fermentation medium, and; (iii) recovering the biologically active botulinum neurotoxin from the fermentation medium, using an anion exchange chromatography media followed by use of a cation exchange chromatography media, wherein the botulinum neurotoxin recovered has a potency of at least about $2.0 \times 10^7$ units/mg of botulinum neurotoxin, preferably about $2.4 \times 10^7$ units/mg of botulinum neurotoxin to about $5.9 \times 10^7$ units/mg of botulinum neurotoxin, in some embodiments at least about $4.4 \times 10^7$ units/mg of botulinum neurotoxin, the botulinum neurotoxin comprises one ng or less than one ng of residual nucleic acid for each mg of the botulinum neurotoxin, and steps (i) to (iii) are completed in one week or less, and; (b) compounding the botulinum neurotoxin with at least one suitable excipient, thereby making a substantially APF pharmaceutical composition. In a particular embodiment, the compounding step comprises the step of drying the botulinum neurotoxin by a process selected from the group of processes consisting of freeze drying, lyophilization and vacuum drying and wherein the suitable excipient is selected from the group consisting of albumin, human serum albumin, recombinant human serum albumin, gelatin, sucrose, trehalose, hydroxyethyl starch, collagen, lactose, sucrose sodium chloride, polysaccharide, caprylate, polyvinylpyrrolidone and sodium. Accordingly, one aspect our invention also provides substantially APF pharmaceutical compositions made by compounding the biologically active botulinum neurotoxin obtained by the processes and systems herein disclosed.

Additionally, our invention also includes a method for treating a condition in a patient, the method comprising the step of administering to the patient a therapeutically effective amount of a pharmaceutical composition made by methods for making a substantially APF pharmaceutical composition in which the active ingredient is a biologically active botulinum neurotoxin obtained by the APF processes (i.e. IAPF and FAPF processes) herein disclosed. Examples of conditions to be treated are selected from the group consisting of a headache, a migraine headache, tension headache, a sinus headache, a cervicogenic headache, a sweating disorder, axillary hyperhidrosis, palmar hyperhidrosis, plantar hyperhidrosis, Frey's syndrome, a hyperkinetic skin line, a facial wrinkle, glabellar lines, crow's feet, marionette lines, a nasolabial fold, a skin disorder, achalasia, strabismus, chronic anal fissure, blepharospasm, musculoskeletal pain, fibromyalgia, pancreatitis, tachycardia, prostatic enlargement, prostatitis, urinary retention, urinary incontinence, overactive bladder, hemifacial spasm, tremors, myoclonus, gastrointestinal disorders, diabetes, sialorrhea, detrusor-sphincter dyssynergia, post stroke spasticity, wound healing, juvenile cerebral palsy, smooth muscle spasm, restenosis, a focal dystonia, epilepsy, cervical dystonia, thyroid disorder, hypercalcemia, an obsessive compulsive disorder, arthritic pain, Raynaud's syndrome, striae distensae, peritoneal adhesion, vasospasms, rhinorrhea, muscle contracture, an injured muscle, laryngeal dystonia, writer's cramp and carpel tunnel syndrome, for example.

In one embodiment, a method for treating a condition in a patient, the method comprising the step of locally administering to the patient an effective amount of a substantially APF pharmaceutical composition made by a method including the steps of: (a) obtaining a biologically active botulinum neurotoxin by (i) providing a fermentation medium which is substantially free of an animal product; (ii) fermenting Clostridium botulinum bacteria in the fermentation medium, and; (iii) recovering the biologically active botulinum neurotoxin from the fermentation medium, using an anion exchange chromatography media followed by use of a cation exchange chromatography media, wherein the botulinum neurotoxin recovered has a potency of at least about $2.0 \times 10^7$ units/mg of botulinum neurotoxin, the botulinum neurotoxin comprises one ng or less than one ng of residual nucleic acid for each mg of the botulinum neurotoxin, and steps (i) to (iii) are completed in one week or less, and; (b) compounding the botulinum neurotoxin with at least one suitable excipient, thereby making a substantially APF pharmaceutical composition, whereby local administration of the substantially APF pharmaceutical composition treats the condition.

Local administration of therapeutically effective amounts of a pharmaceutical compositions, comprising a biologically active botulinum neurotoxin provided by the IAPF process/ systems/method herein disclosed, can be repeated at intervals of from about 2 months to about 6 months or at intervals of about 2 months to about 3 months, for example. Exemplary useful dosages locally administered to the patient of a therapeutically effective amount of a substantially APF pharmaceutical composition made in accordance with the present disclosure, can have botulinum neurotoxin unit amounts of between about 0.01 unit and about 10,000 units. In particular instances, the botulinum neurotoxin is administered in an amount of between about 0.01 unit and about 3000 units. In particular examples, the biologically active botulinum neurotoxin that is the active pharmaceutical ingredient in the pharmaceutical composition is botulinum neurotoxin type A or type B, for example.

Our invention includes a substantially APF process, utilizing chromatography, for obtaining a biologically active botulinum neurotoxin. The process can comprise the sequential steps of providing a substantially APF fermentation medium, followed by fermenting *Clostridium botulinum* bacteria in the fermentation medium and recovering the biologically active botulinum neurotoxin from the fermentation medium using an anion exchange chromatography media followed by use of a cation exchange chromatography media to thereby obtain the biologically active botulinum neurotoxin from the substantially APF chromatographic process. The recovering step can also include the use of a hydrophobic interaction media after the use of cation exchange chromatography media. The biologically active botulinum neurotoxin obtained can be a botulinum neurotoxin complex or a botulinum toxin neurotoxic component isolated therefrom with a molecular weight of about 150 kDa free of the complexing proteins of a botulinum toxin complex. The APF processes (utilizing 2-columns (IAPF), e.g. anion followed by cation chromatography; or 3-columns (FAPF), e.g. anion followed by cation followed by hydrophobic interaction chromatography) can be used to obtain a biologically active botulinum neurotoxin such as botulinum neurotoxins type A, B, $C_1$, D, E, F and G. The botulinum neurotoxin obtained is preferably a botulinum neurotoxin type A complex.

In one aspect of our invention, the amount of fermentation medium used can comprise from about 2 L to about 75 L of substantially APF fermentation medium, preferably from about 2 L to about 30 L of substantially APF fermentation medium. As an example, from about 100 mg to about 5 grams, preferably from about 100 mg to about 3 grams, more preferably from about 100 mg to about 1 gram of the biologically active botulinum neurotoxin is obtained from the process. As an example, from about 20 mg to about 100 mg or from about 20 mg to about 80 mg of the biologically active neurotoxin may be obtained per liter of the fermentation medium used. Fermentation medium can comprise vegetable derived protein product, yeast extract and glucose, for example. As an example, the fermentation medium comprises about 5% w/v or less of a vegetable derived protein product. In yet another example, the fermentation medium comprises about 2% w/v or less of a yeast extract. In a further embodiment, the fermentation medium comprises about 2% w/v or less of glucose. In a particular example, fermentation medium comprises about 5% w/v or less of a vegetable-derived protein product, about 2% w/v or less of a yeast extract and about 2% w/v or less of glucose, the vegetable-derived protein product, yeast extract and glucose being in any ratio in accordance with the recited w/v percentage amounts. In some embodiments, the fermenting step proceeds for between about 60 hours to about 80 hours.

In one embodiment, a substantially APF process utilizing chromatography for obtaining a biologically active botulinum neurotoxin, the process comprising the following sequential steps, is provided where culturing *Clostridium botulinum* bacteria in a substantially APF culture medium, then fermenting *Clostridium botulinum* bacteria from the culture medium in about 2 L to about 75 L of a substantially APF fermentation medium, more preferably in about 2 L to about 30 L of a substantially APF fermentation medium, where at least one of the substantially APF culture medium and substantially APF fermentation medium include a vegetable protein, followed by harvesting the fermentation medium by removing cellular debris present in the fermentation medium and concentrating the harvested fermentation medium by filtration, and diluting the concentrated fermentation medium by adding a buffer. Once buffered, a first contacting step is executed, in which the diluted harvested fermentation medium is contacted with an anion exchange media so that the biologically active botulinum neurotoxin is associated with the anion exchange media, then eluting the captured botulinum neurotoxin from the anion exchange media proceeds to thereby obtain a first eluent, followed by a second contacting step in which the first eluent is contacted with a cation exchange media to remove impurities from the first eluent, thereby obtaining a second eluent; which is then processed, such as by UF and/or DF; and then filtering the processed second eluent, thereby obtaining biologically active botulinum neurotoxin using a substantially APF process that utilizes chromatography.

As an example, the time for completion of the process, from culturing the bacteria to obtaining the biologically active botulinum neurotoxin can be from between about 50 hours to about 150 hours, more preferably about 80 hours to about 120 hours, for example. In particular embodiments, the culture medium comprises no more than about 4% w/v of a vegetable-derived protein product, in another, the culture medium comprises no more than about 2% w/v of a yeast extract and yet in still another, the culture medium comprises no more than about 2% w/v glucose. The culture medium can comprise the vegetable-derived protein product, yeast extract and glucose in any ratio in accordance with the recited w/v percentage amounts. In a specific example, the pH level of the culture medium can be from about pH 6.5 to about pH 8.0, preferably about pH 6.8 to about pH 7.6, more preferably 7.3 at the commencement of the culturing step. The culturing step can be carried out for between about 8 hours and about 14 hours, about 10 hours to 12 hours, preferably about 11 hours, at a temperature of from about 33° C. to about 37° C., preferably at about 34.5° C., in an anaerobic chamber. In a particular example, the anaerobic chamber can contain an integral high efficiency particular filter within its workspace, where culturing is conducted. The fermenting step can be carried out for between about 60 hours and about 80 hours, preferably about 72 hours at a temperature of from about 33° C. to about 37° C., preferably at 35° C. In accordance with one aspect of our invention, the harvesting step can remove at least about 80% of RNA and DNA contained in the fermentation medium and the anion exchange media can remove all measurable remaining DNA and RNA (below limit of detection) in the harvested fermentation medium. In another aspect, the harvesting step can be carried out for between about 1 hour and about 3 hours, preferably about 2.5 hours. In particular examples, the harvesting step can be carried out until 75% of the original fermentation medium volume has been collected. In one aspect of an embodiment, the concentrating step can be carried out for between about 30 minutes and about 2 hours, preferably about 0.75 hour. In another aspect, the diluting step dilutes the harvested fermentation medium back up to the initial weight of the fermentation medium at the commencement of the harvesting step. A first contacting step can be carried out for between about 4 hours and about 5 hours, for example. In one example, the first eluate from the anion exchange resin is collected at spectrophotometer readings of from about 150 mAU or greater, until spectrophotometer readings at 280 nm decrease from peak apex back to about 150 mAU. The second contacting step can be carried out for between 1 hour and about 3 hours, preferably for about 2 hours. This second eluate can be collected from the cation exchange resin at spectrophotometer readings from about 100 mAU or greater, until spectrophotometer readings decrease from peak apex to about 100 mAU, for example. A step of processing this second eluent by concentration and diafiltration can be carried out for between about 1 hour and about 2 hours, preferably for about 1.5 hours. In a particular embodiment, the filtering step includes bioburden reduction by passing the second eluent through a bioburden reduction filter. The bioburden reduction filter can have a pore size of from about 0.1 μm to about 0.3 μm, preferably 0.2 μm. In particular embodiments, the process can further comprise a third contacting step after the second contacting step, by contacting the second eluent to a hydrophobic interaction media to further remove impurities from the second eluent and to thereby obtain a third eluent. This third contacting step can be carried out for between about 1 hour and 3 hours, preferably for about 2 hours. The third eluate can be collected from the hydrophobic interaction media at spectrophotometer readings from about 50 mAU or greater, until spectrophotometer readings decrease from the peak apex back to about 50 mAU, for example. Where there is a third contacting step, the step of processing by concentration and diafiltration is applied to the third eluent and is carried out for between about 2 hours and about 4 hours. Bioburden reduction by passing the eluent that is concentrated and diafiltered (either from a 2 or 3-column process utilized) through a bioburden reduction filter can accordingly be performed. In particular embodiments, the process further comprises a step of freezing the biologically active botulinum neurotoxin obtained.

In particular embodiments, the substantially APF culture medium comprises a volume of between about 100 mL and about 500 mL. Particular culturing steps are initiated by introducing between about 100 μL and about 500 μL of a Clostridium botulinum-containing APF working cell bank media to the substantially APF culture medium. The culturing step can then take place in an anaerobic chamber for at least about 8 hours, preferably about 11 hours, at a temperature of about 34.5° C.±1° C., for example. In one example, the working cell bank media can have a viable cell count assay of at least about 1×10⁴ colony forming units/mL of working cell bank media, for example about 1×10⁵ to about 5×10⁷ colony forming units/mL of working cell bank media, and the Clostridium botulinum bacterium in the working cell bank can have been selected to have a substantially uniform morphology.

In one embodiment, the working cell bank media includes about 20% by volume glycerol, such as sterile glycerol, for example. The working cell bank media can be made by (a) growing Clostridium botulinum bacterium in an APF medium containing about 2% w/v soy peptone, about 1% w/v yeast extract, and about 1% w/v glucose in an anaerobic chamber, at a temperature of about 34.5° C.±1° C. until an optical density of an aliquot of the medium measured at a wavelength of about 540 nm is about 2.5±1.0 AU, and; adding glycerol to obtain a concentration of glycerol in the medium of about 20%, thereby obtaining a working cell bank. A storage form of the working cell bank can be prepared by freezing the working cell bank at about below −135° C., for example. The storage form of the working cell bank, for use in an exemplary process in accordance with the present disclosure, can be thawed at ambient temperature and used to initiate the culturing step.

The culturing step can be carried out for between about 8 hours and about 14 hours, preferably about 11 hours at a temperature of from about 33° C. to about 37° C., preferably at about 34.5° C., in an anaerobic chamber, such as, for example an anaerobic chamber/cabinet having an integrated high efficiency particulate air (HEPA) filter, preferably within its workspace. The fermenting step can be carried out for between about 20 hours and about 80 hours, preferably from about 60 hours to about 80 hours, more preferably for about 72 hours at a temperature of from about 33° C. to about 37° C., preferably at 35° C. The process can further comprise, for example and before the culturing step, a step of allowing for oxidative reduction of the substantially APF culture medium by exposing the medium to the atmosphere of an anaerobic chamber. The process can also include before the fermenting step, a step of allowing for oxidative reduction of the substantially APF fermentation medium by also exposing the fermentation medium to the atmosphere of an anaerobic chamber. As one example, the step of allowing for oxidative reduction of the substantially APF culture medium can be carried out for between about 10 hours and about 14 hours in the anaerobic chamber. Similarly, the step of allowing for oxidative reduction of the substantially APF fermentation medium in the fermentor can be carried out for between about 10 hours and about 14 hours before the beginning of the fermenting step. In one embodiment, an APF process, including chromatography, for obtaining a biologically active botulinum neurotoxin is disclosed, comprising the following sequential steps of adding Clostridium botulinum bacteria from an APF working cell bank to an APF culture medium; culturing the Clostridium botulinum bacteria in the culture medium; fermenting Clostridium botulinum bacteria from the culturing step in an APF fermentation medium until Clostridium botulinum cell lysis occurs; harvesting the APF fermentation culture to provide a harvested fermentation medium; subjecting the harvested fermentation medium to concentration by filtration; diluting the filtered fermentation medium by addition of a buffer to obtain a diluted fermentation medium; a first contacting step in which the diluted fermentation medium is contacted with a capture chromatography media, wherein the capture chromatography media is an anion exchange media; a second contacting step wherein an eluent from the first contacting step is contacted with a polishing chromatography media, wherein the polishing chromatography media is a cation exchange media, and filtering the eluent from the second contacting step, thereby obtaining biologically active botulinum neurotoxin by the improved APF process. In particular embodiments, the process can further comprise the step of conducting a third contacting step, after the second contacting step and before the filtering step, by contacting eluent from the second contacting step with a hydrophobic interaction media. The Clostridium botulinum lysis phase can occur between about 35 hours and about 70 hours after commencement of the fermenting step, for example. The fermentation medium can have a volume of between about 2 L and about 75 L, between about 2 L and about 30 L, or between about 2 L and 20 L of fermentation medium, for example. The whole of this process can be carried out for between about 50 hours to about 150 hours, more preferably from about 80 hours to about 120 hours. The biologically active botulinum neurotoxin thus obtained by this process can have a potency of about $2.4 \times 10^7$ to about $5.9 \times 10^7$ units/mg of biologically active botulinum neurotoxin, for example.

In accordance with one aspect, at the end of fermentation, from about 40 mg to about 85 mg of botulinum neurotoxin per liter of fermentation medium can be obtained. Subsequent to various stages of processing (filtration/chromatography/filtration runs), from about 30 mg to about 60 mg of botulinum neurotoxin per liter of fermentation medium; from about 5 mg to about 25 mg of botulinum neurotoxin per liter of fermentation medium; from about 6 mg to about 20 mg of botulinum neurotoxin per liter of fermentation medium can be obtained.

As one embodiment, the pH of the fermentation medium can be adjusted to be between about pH 6.0 and about pH 8, preferably between about pH 6.8 and about pH 7.6 at commencement of the fermenting step, more preferably about pH 7.3. As another example, substantially APF chromatographic process for obtaining a biologically active botulinum neurotoxin is also provided, the process comprising the steps of obtaining a substantially APF fermentation medium containing a botulinum neurotoxin; contacting the medium with an anion exchange chromatography resin to provide a purified eluent containing a botulinum neurotoxin; contacting the eluent with an cation exchange chromatography resin to thereby obtain a further purified eluent, and filtering the further purified eluent to thereby obtain a biologically active botulinum neurotoxin purified from a substantially APF chromatographic process. In particular configurations, an anion chromatography column can be utilized which contains from about 600 mL to about 800 mL of anion exchange chromatography resin. The anion chromatography column can have a diameter of about 8 cm to about 10 cm and an anion exchange chromatography resin bed height in the column of from about 9 cm to about 16 cm, for example. A flow rate of fermentation medium through the anion exchange chromatography resin can be from about 140 cm/hour to about 250 cm/hour, or from about 150 cm/hour to about 160 cm/hour, for example. In another aspect, from about 150 mL to about 300 mL of cation exchange chromatography resin in a chromatography column can be utilized in the process, where the cation chromatography column has a diameter of about 5 cm to about 8 cm and a cation exchange chromatography resin bed height of from about 5 cm to about 11 cm, for example. The process can include at least one of a diafiltration step and/or a bioburden reduction step. The bioburden reduction step can utilize a capsule filter. The diafiltration of purified eluent is preferably performed before a bioburden reduction step. In one example, the step of diafiltering the further purified eluent is either preceded or followed by adjusting the concentration of the diafiltered further purified eluent, and passing the concentration-adjusted diafiltered further-purified eluent through a bioburden reduction filter. The process can provide a botulinum neurotoxin obtained having potency, as determined by a mouse $LD_{50}$ bioassay, of from at least about $2.0 \times 10^7$ units/mg of botulinum toxin, such as about $2.4 \times 10^7$ to about $6.0 \times 10^7$ units/mg of botulinum neurotoxin. Exemplary recovery at the end of the process of from about 4 mg to about 25 mg of botulinum toxin can be recovered per liter of fermentation media, for example.

In another embodiment, an essentially APF process for purifying a biologically active botulinum neurotoxin can comprise the steps of obtaining from about 2 L to about 30 L an APF fermentation medium that includes a botulinum neurotoxin; harvesting the APF fermentation medium step to provide a harvested APF fermentation medium; performing anion exchange chromatography upon the harvested APF fermentation medium to thereby provide a first eluent; contacting the eluent from the anion exchange chromatography with cation exchange chromatography media to perform cation exchange chromatography to thereby provide a second eluent; and filtering the second eluent from the cation exchange chromatography media, thereby obtaining a purified botulinum neurotoxin, wherein the purified botulinum neurotoxin obtained has a potency of from about $2.4 \times 10^7$ to about $5.9 \times 10^7$ units/mg of biologically active botulinum neurotoxin and can be obtained in a quantity of between about 4 mg to about 25 mg per liter of APF fermentation medium used.

Our invention also comprises a compounding method for making a substantially APF pharmaceutical composition in which the active ingredient is a biologically active botulinum neurotoxin, comprising the steps of obtaining a biologically active botulinum neurotoxin by (i) providing a fermentation medium which is substantially free of animal products; (ii) fermenting *Clostridium botulinum* bacteria in the fermentation medium, and (iii) recovering the biologically active botulinum neurotoxin from the fermentation medium, using an anion exchange chromatography media followed by use of a cation exchange chromatography media; and then compounding the botulinum neurotoxin with at least one suitable excipient to thereby making a substantially APF pharmaceutical composition. In one example, the method includes the step of drying the compounded botulinum neurotoxin and at least one suitable excipient to obtain a stable form for shipment or storage, by freeze drying or lyophilization or vacuum drying, in which the active ingredient is the biologically active botulinum neurotoxin, where the fermentation medium comprises a protein product obtained from a vegetable. The vegetable from which the protein product can obtained can be a soy, corn or malt, debittered seed of *Lupinus campestris*, or hydrolyzed products therefrom. The botulinum neurotoxin obtained can have a potency between about $2.0 \times 10^7$ units/mg of botulinum neurotoxin to about $6.0 \times 10^7$ units/mg of botulinum neurotoxin. The botulinum neurotoxin is selected from the group consisting of botulinum neurotoxins types A, B, $C_1$, D, E, F and G, preferably botulinum neurotoxin type A. In particular instances the botulinum neurotoxin is obtained as a botulinum toxin neurotoxic component with a molecular weight of about 150 kDa free of the complexing proteins of a botulinum toxin complex. In particular embodiments, the suitable excipient is selected from the group consisting of albumin, human serum albumin, recombinant human serum albumin, gelatin, sucrose, trehalose, hydroxyethyl starch, collagen, lactose, sucrose, amino acid, sodium chloride, potassium chloride, polysaccharide, caprylate, polyvinylpyrrolidone and potassium citrate. Obtaining the biologically active botulinum neurotoxin can further comprise the step of using a hydrophobic interaction media following use of the cation exchange media. In particular examples, vacuum drying takes place at a temperature of about 20° C. to about 25° C. In some embodiments, the vacuum drying takes place at a pressure of about 70 mmHg to about 90 mmHg, for example. The time for vacuum drying can be from about 4 hours to about 5 hours, for example.

Particular aspects of the present disclosure are directed to providing a pharmaceutical composition, which can, for example, comprise a biologically active botulinum neurotoxin complex and an excipient is selected from the group consisting of albumin, human serum albumin, recombinant human serum albumin, gelatin, sucrose, trehalose, hydroxyethyl starch, collagen, lactose and sucrose, where the pharmaceutical composition is essentially free of nucleic acid.

In particular examples, a pharmaceutical composition is provided that comprises a biologically active botulinum neurotoxin wherein the botulinum neurotoxin obtained has a potency between about $2.0 \times 10^7$ to about $6.0 \times 10^7$ units/mg of biologically active botulinum neurotoxin and at least one excipient, where the composition comprises less than about 12 ppm of nucleic acid, preferably less than 1 ppm of nucleic acid per mg of botulinum neurotoxin complex.

In a particular embodiment, a substantially APF chromatographic process for obtaining a biologically active botulinum neurotoxin comprises the following sequential steps of: culturing *Clostridium botulinum* bacteria in a substantially APF culture medium for between about 10 hours and about 12 hours, or until a biomass measurement of culture medium has an optical density, at a wavelength of about 540 nanometers (nm), of between about 0.8 AU and about 4.5 AU; fermenting *Clostridium botulinum* bacteria from the culture medium in a substantially APF fermentation medium for between about 65 hours to about 75 hours or until a biomass measurement is taken at the end of fermentation by measuring the optical density of the fermentation medium using a online biomass probe at a wavelength of about 890 nm is between about 0.05 AU and about 0.7 AU; harvesting the fermentation medium for about 2.5 hours, whereby cellular debris in the fermentation medium is removed and the weight of fermentation medium is reduced to about three quarters of its starting weight at the beginning of the harvesting step; concentrating the harvested fermentation medium by tangential flow filtration to about one quarter of its starting volume at the beginning of the harvesting step; diluting the concentrated fermentation medium by adding a buffer, wherein the concentrating and diluting steps take place for between about 0.5 hour to about 2 hours, whereby during concentration the fermentation medium is reduced to about one quarter of its starting weight at the beginning of the harvesting step, and is then diluted, by the addition of the buffer, back up to its original starting weight at the beginning of the harvesting step; contacting the diluted fermentation medium with a capture chromatography media, to capture the biologically active botulinum neurotoxin, for a time period of about 4 hours to about 5 hours; contacting eluent from the capture chromatography media with a first polishing chromatography media to conduct a first polishing run to remove impurities therefrom for a time period of about 1.5 hours to about 2.5 hours; conducting a second polishing run by passing eluent from the polishing chromatography media through a hydrophobic interaction media for a time period of about 1.5 hours to about 2.5 hours; processing eluent from the hydrophobic interaction media by diafiltration, for a time period of about 1 hour to about 4 hours; and filtering the processed eluent through a bioburden reduction filter, for about 0.5 hour, thereby obtaining biologically active botulinum neurotoxin.

In another aspect, a substantially APF chromatographic system for obtaining a biologically active botulinum neurotoxin is disclosed, the system comprising: a first apparatus for culturing *Clostridium botulinum* bacteria, the first apparatus capable of containing a substantially APF culture medium; a second apparatus for fermenting *Clostridium botulinum* bacteria which have been cultured in the first apparatus, the second apparatus capable of containing a substantially APF fermentation medium; a third apparatus for harvesting the fermentation medium; a fourth apparatus for carrying out concentrating and diluting the harvested medium from the third apparatus; the fourth apparatus comprising tangential flow filtration (TFF); a fifth apparatus for carrying out a first purification of the botulinum neurotoxin from the concentrated and diluted medium, the fifth apparatus comprising an anion exchange chromatography media, thereby obtaining a first purified botulinum neurotoxin; and a sixth apparatus for carrying out a second purification of the first purified botulinum neurotoxin, the sixth apparatus comprising a cation exchange chromatography media, and thereby obtaining a second purified botulinum neurotoxin.

In a particular embodiment, the system can further comprise a seventh apparatus for carrying out a further purification, by purifying the second purified botulinum neurotoxin obtained from the sixth apparatus, wherein the seventh apparatus comprises a hydrophobic interaction media, thereby obtaining a third purified botulinum neurotoxin. The system can also further be comprised of an eighth apparatus having a filtration membrane for filtering eluent from the sixth or seventh apparatus.

In still yet another embodiment, a chromatography column with a diameter of between about 8 cm and about 15 cm contains the anion exchange chromatography media and the anion exchange chromatography media can have a bed height in the column of between about 8 cm and about 15 cm, for example. In still another example, the system's fourth apparatus comprises a chromatography column that is operated at a flow rate of between about 125 cm/hour and about 200 cm/hour, and the column can have a column volume between about 500 mL and about 1 L. In one aspect, the fifth apparatus can have a column volume of from about 50 mL and about 500 mL, and a bed height of from about 8 cm and about 15 cm, for example. In some examples, the fifth apparatus' chromatography column has a column diameter from about 2 cm and about 10 cm, for example. The fifth apparatus' chromatography column can have an exemplary flow rate of between about 100 cm and about 200 cm/hour. The seventh apparatus of the system can comprise a filtration membrane.

In another embodiment, the system can further comprise a ninth apparatus, the ninth apparatus comprising an anaerobic chamber for providing an anaerobic atmosphere where the first apparatus for culturing *Clostridium botulinum* bacteria is contained therein. This ninth apparatus preferably includes an integrated high efficiency particulate air (HEPA) filter located within its chamber/workstation. The second apparatus of the system (for fermentation) can include at least one probe for detecting oxidation-reduction potential or pH or optical density. In a particular example, an at least one disposable probe is selected from the group consisting of a reduction-oxidation probe, a pH probe and a turbidity probe. A eighth apparatus of the system can comprise a tangential flow filtration apparatus for concentration and buffer exchange. In a further embodiment, the system can comprise an tenth apparatus that includes a bioburden reduction apparatus for reducing bioburden. In one example, the bioburden reduction apparatus comprises a filter having a pore size of about between about 0.1 µm and 0.3 µm, preferably 0.2 µm. The system can also include a eleventh apparatus for use after obtaining the second purified botulinum neurotoxin, for storing the purified botulinum neurotoxin. In one example, this storage apparatus provides a storage temperature between about −25° C. to about −80° C.

In another aspect, a biologically active botulinum toxin is provided by an APF process having the following steps of providing a substantially APF fermentation medium; fermenting a *Clostridium botulinum* bacteria in the fermentation medium; recovering the biologically active botulinum neurotoxin from the fermentation medium using an anion exchange chromatography media followed by use of a cation exchange chromatography media, where the biologically active botulinum toxin obtained has a potency between about $2.0 \times 10^7$ units/mg of botulinum neurotoxin to about $6.0 \times 10^7$ units/mg of botulinum neurotoxin. In one embodiment, the process further comprises the step of further purifying the botulinum neurotoxin by using a hydrophobic interaction media following use of the cation exchange media.

In accordance with another aspect, a method for treating a condition in a patient is provided, utilizing a pharmaceutical composition comprising the botulinum neurotoxin obtained in accordance with the methods herein disclosed. A condition can include a disease, ailment, sickness, or cosmetic deformity or appearance. In one example, the method of treating a condition in a patient comprises the step of administering to the patient a therapeutically effective amount of a pharmaceutical composition comprising a botulinum neurotoxin and at least one suitable excipient, where the botulinum toxin has a potency of about 1 unit≥ about 0.02 picograms to thereby treat the condition of the patient.

In a particular example, the botulinum neurotoxin for treating these conditions can be obtained by a process of culturing *Clostridium botulinum* bacteria in a substantially APF culture medium; obtaining a substantially APF fermentation medium containing the botulinum neurotoxin; contacting the medium with an anion exchange chromatography media to provide a purified eluent containing the botulinum neurotoxin; contacting the eluent with an cation exchange chromatography media to thereby obtain a further purified eluent, and filtering the further purified eluent to thereby obtain the biologically active botulinum neurotoxin purified from a substantially APF chromatographic process.

In one embodiment a substantially APF chromatographic system for obtaining a biologically active botulinum neurotoxin is included, the system comprising a first apparatus for anaerobic culturing *Clostridium botulinum* bacteria, the first apparatus capable of containing from about 200 mL to about 1 L of a substantially APF culture medium; a second apparatus for anaerobic fermentation of *Clostridium botulinum* bacteria which has been cultured in the first apparatus, the second apparatus capable of containing from about 5 L to about 75 L, or from about 2 L to about 75 L, or from about 2 L to about 30 L of a substantially APF fermentation medium and including at least one disposable probe selected from the group consisting of a reduction-oxidation probe, a pH probe and a turbidity probe; a ninth apparatus for providing an anaerobic atmosphere and capable of containing the first apparatus, the ninth apparatus comprising an anaerobic chamber having an integrated high efficiency particulate air filter within the chamber, wherein said chamber can contain the first apparatus for anaerobic culturing *Clostridium botulinum* bacteria; a third apparatus for harvesting the fermentation medium; a fourth apparatus for carrying out concentration and dilution of the harvested medium, a fifth apparatus for carrying out a first purification of botulinum neurotoxin obtained from the fourth apparatus, the fifth apparatus comprising an anion exchange chromatography media, thereby obtaining a first purified botulinum neurotoxin; a sixth apparatus for carrying out a second purification of the first purified botulinum neurotoxin, the sixth apparatus comprising a cation exchange chromatography media, thereby obtaining a second purified botulinum neurotoxin; a seventh apparatus carrying out a third purification of the second purified botulinum neurotoxin, the seventh apparatus comprising hydrophobic interaction media, thereby obtaining a third purified botulinum neurotoxin; and an eighth apparatus for concentration and buffer exchange of the third purified botulinum neurotoxin, the eighth apparatus comprising a TFF membrane.

In particular examples, the fermentation medium comprises no more than about 5% w/v of a vegetable-derived protein product, no more than about 2% w/v of a yeast extract and no more than about 2% w/v glucose, and where the pH level of the fermentation medium is from about pH 6.8 to about 7.6, preferably about pH 7.3 at the start of an about 72 hour fermenting step, for example. In one embodiment, the method can further comprise the step of contacting the further purified eluent with a hydrophobic interaction media to obtain an even further purified eluent containing the botulinum neurotoxin. In a particular example, the method of treating the conditions can be by using a botulinum neurotoxin that is obtained as a botulinum toxin neurotoxic component with a molecular weight of about 150 kDa free of the complexing proteins of a botulinum toxin complex. Exemplary administration steps can be selected from the group of administration routes consisting of intramuscular, intradermal, subcutaneous, intraglandular, intrathecal, rectal, oral and transdermal administration, and the botulinum neurotoxin is selected from the group consisting of botulinum toxin type A, B, $C_1$, D, E, F or G. Preferably, the botulinum neurotoxin is botulinum neurotoxin type A.

In some examples, the system can facilitate a process whereby a biologically active botulinum neurotoxin complex can be obtained for use as part of pharmaceutical composition that comprises less than about 12 ng of nucleic acid per mg of botulinum neurotoxin complex, preferably below 1 ng of nucleic acid per mg of botulinum neurotoxin complex, more preferably having no measurable a nucleic acid (e.g. below a limit of detection).

DESCRIPTION

Figures 1A, 1B:
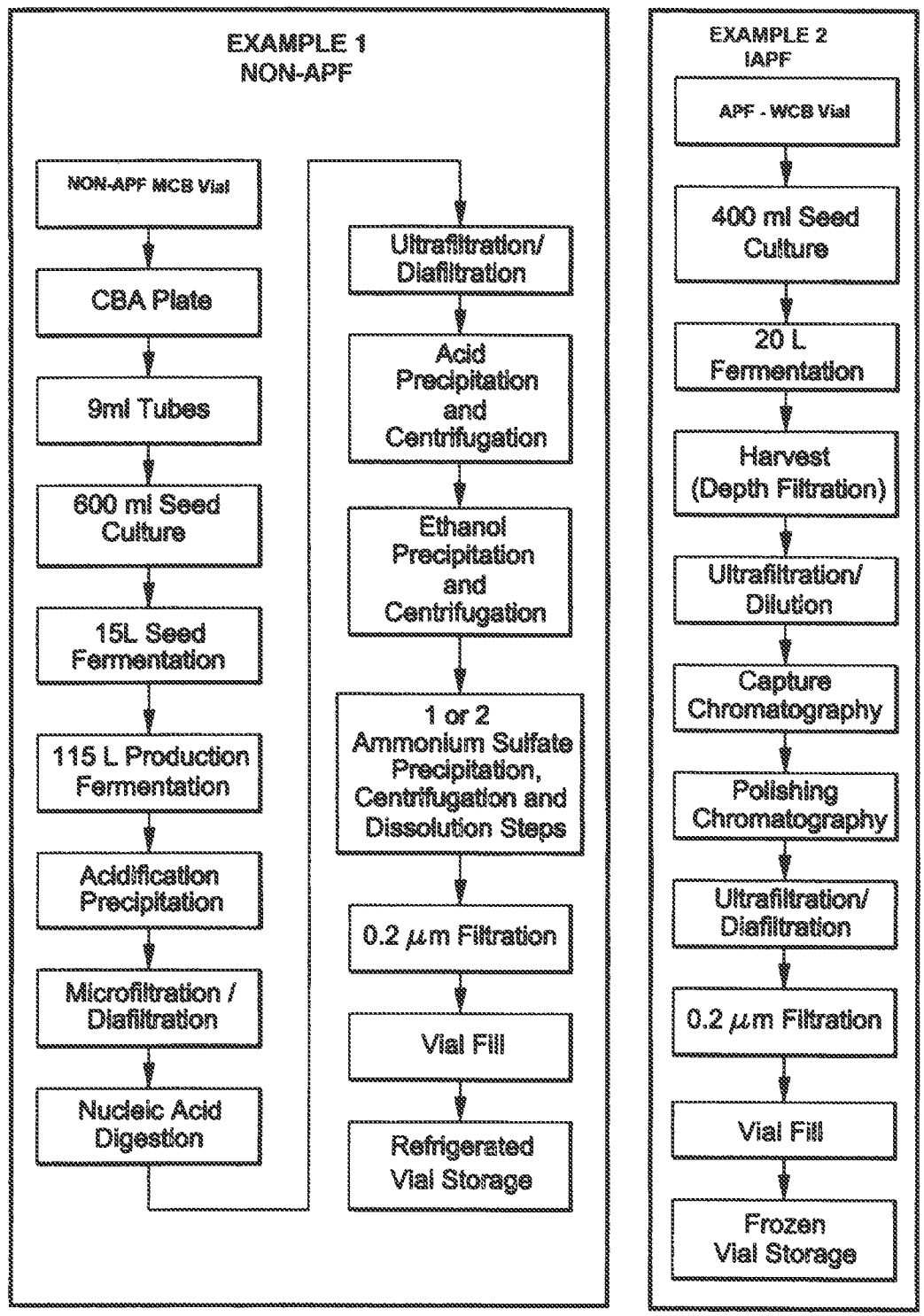
FIG. 1A is a flow chart showing major steps in the Example 1 NAPF process.
FIG. 1B is a flow chart showing major steps in the Example 2 IAPF process, wherein the capture and polishing chromatography steps can utilize either a 2-columns (anion exchange followed by cation exchange) or 3-columns (FAPF) (anion exchange followed by cation exchange followed by a hydrophobic interaction column).

Our invention is based on the discovery that a high potency, high purity biologically active Clostridial neurotoxin, such as a botulinum neurotoxin, can be obtained by use of a simple, fast and economical APF chromatographic system and process. Significantly, use of our system and process can result in a purified botulinum neurotoxin comprising 1 ng (or less than 1 ng) of nucleic acid (RNA and DNA) impurities per 1 mg of the purified botulinum neurotoxin obtained, even though no animal derived enzymes, such as RNase and DNase, are used to purify the fermented botulinum neurotoxin. For example, use of our system and process can result in a purified botulinum neurotoxin comprising less than about 0.6 ng of nucleic acid (RNA and DNA) impurities per milligram of purified botulinum neurotoxin, obtained. The botulinum neurotoxin obtained can be a botulinum toxin type A complex, such as a 300 kDa, 500 kDa or 900 kDa (approximate molecular weights) complex or mixtures thereof. The botulinum neurotoxin obtained can also be a botulinum toxin type neurotoxic component (i.e. without the complex proteins) with a molecular weight of about 150 kDa. The botulinum neurotoxin can be any one of the serotypes A, B, C, D, E, F or G or mixtures thereof. Additionally, the improved systems and processes can be practiced in conjunction with a recombinant, hybrid, chimeric or modified botulinum toxin (light chain, heavy chain, or both chains together).

An important aspect of our invention is use of an anion exchange (capture) media chromatography followed by use of cation exchange (polishing) media chromatography to purify botulinum neurotoxin from an APF fermentation medium in which *Clostridium botulinum* bacterium have been fermented. We found that use of anion exchange followed by use of cation exchange chromatography media provides an effective and rapid method for obtaining high purity, high yield botulinum neurotoxin. Previously, it had been thought that use of anion exchange chromatography has a detrimental effect on gel banding patterns of botulinum neurotoxin, thereby discouraging use of anion exchange chromatography for botulinum neurotoxin purification. See e.g. U.S. Pat. No. 7,452,697 at column 55, lines 53-57.

Another important aspect of our invention is that it results in high purity botulinum neurotoxin (i.e. ≤1 ng nucleic acid/mg botulinum neurotoxin obtained), as set forth above. A further important aspect of our invention is that whereas the known Schantz process requires several weeks (i.e. typically about 18 to about 22 days) to culture, ferment and purify the botulinum neurotoxin, a system and process within the scope of our invention permits all culturing, fermentation and purification steps to be completed in one week or less. In a preferred embodiment of our invention all culturing, fermentation and purification steps can be completed in six days or less. In a more preferred embodiment of our invention all culturing, fermentation and purification steps can be completed in about four days or less (e.g. within about 80 to about 144 hours or within a time/range therebetween). We invented this rapid, more embodiment of our invention by developing an eight or nine step process (and the system for accomplishing the process) and by finding that each of the eight or nine steps in a particular embodiment can be completed within the time periods set forth below:

about 8 hours to about 14 hours for culturing;
about 60 hours to about 80 hours for fermenting;
about 2.5 hours for harvesting;
about 2 hours to about 4 hours for concentrating and diluting;
about 4 hours to about 6 hours for anion exchange chromatography (this includes time for eluting captured botulinum toxin);
about 2 hours for cation exchange chromatography;
about 2 hours for an optional third chromatography step (i.e. hydrophobic interaction chromatography;
about 2 hours to about 4 hours for concentration and diafiltration, and;
about ½ hour for further filtration. Thus, the total time required to complete our 8 or 9 step rapid, more preferred embodiment of our invention is from about 75 hours to about 150 hours.

Our invention is more efficient and time saving. In one aspect, our new process utilizes pre-selected and verified cell lines, and thus does away with the prior art Schantz process steps of plating and growing cells, selecting and harvesting colonies, and step-up cell-line expansion of the harvested colonies (prior to cell culturing and fermentation steps) that were needed to culture and then inoculate fermentation medium. In one aspect, our invention begins straight away with culturing pre-selected cells for inoculation of an APF culture medium, thus saving time and process steps.

Through experimentation we developed two chromatography column ("IAPF") and three column ("FAPF"/"FI-APF") chromatography systems and processes for purifying the botulinum neurotoxin present in the fermentation medium, the fermentation medium resulting from an APF fermentation of *Clostridium botulinum* bacterium. Significantly, while an APF fermentation process can reduce or eliminate animal derived products (such as casein and meat broth) as nutrients from the media used to culture and ferment Clostridial bacteria, known APF fermentation processes are typically followed by one or more purification steps which make use of animal derived products, such as the enzymes DNase and RNase. Our systems and processes for purifying the botulinum neurotoxin present in an APF fermentation medium do not use animal derived enzymes.

Our invention can encompass loading a harvested fermentation medium (e.g. clarified by filtration) onto an anion exchange column such as a POROS® 50HQ anion exchange chromatography resin from Applied Biosystems. In one aspect, a strong anion exchange media can be used, having a base matrix of polystyrene/divinylbenzene and particle diameter of about 50 μm and dynamic capacity (BSA mg/ml) of about 60-70. The anion exchange column captures the Clostridial neurotoxin (such as a botulinum toxin complex) and reduces impurity levels. It was found that an anion exchange column provided an efficient capture of a botulinum toxin complex from harvested fermentation medium with retention of the biological activity of the botulinum toxin complex, while also separating many impurities present with the botulinum toxin in the fermentation medium. A suitable buffer is used to elute the captured (bound) Clostridial neurotoxin from the anion exchange column.

In a two-column embodiment of our invention, eluent (containing the botulinum neurotoxin) from the anion exchange column is loaded onto a cation exchange column to further purify the botulinum neurotoxin from impurities. The cation exchange column can be a POROS® 20HS cation exchange resin from Applied Biosystems. In one aspect, a strong cation exchange media can be used, having a base matrix of polystyrene/divinylbenzene and particle diameter of about 20 μm and dynamic binding capacity (lysozyme mg/ml) of about >75. In a three-column embodiment (FAPF) of our invention, eluent from the cation exchange column is loaded onto a hydrophobic interaction column such as Phenyl Sepharose HP resin from GE Healthcare to further purify the botulinum neurotoxin. In one aspect, a matrix of highly cross-linked agarose beads with a particle size of about 34 μm, which have been derivatized with phenyl groups and have a dynamic binding capacity (chymotrypsinogen mg/ml) of about 45, may be used.

After either the two column or three column process, eluent from the last used column can be further processed to obtain highly purified bulk botulinum toxin complex. Post-chromatography processing steps can include concentration and buffer exchange by ultrafiltration and diafiltration, sterile filtration and preparation of a solution of purified botulinum toxin complex instead of a suspension (prior art), preferably in potassium citrate, and in one example, at a concentration of 10 mM potassium citrate at a pH of about 6.5.

In certain preferred embodiments, the media for the growth (anaerobic culturing and anaerobic fermentation) of *Clostridium botulinum* and production of botulinum toxin can comprise soy-based products to replace animal derived products so that media used are substantially or entirely free of animal-derived products. The culture step increases the quantity of microorganism for subsequent fermentation. Culturing permits dormant, previously frozen bacteria to rejuvenate into actively growing cultures. Additionally, the volume and quantity of viable microorganisms used to inoculate the fermentation medium can be controlled more accurately from an actively growing culture than it can be from a stored, non-propagating *Clostridium botulinum* cell bank. Thus, a sample of a working cell bank in APF media is thawed and placed in the selected APF culture medium. Upon obtaining a suitable level of bacterial growth the culture medium is used to inoculate the fermentation medium. As one example, from about 1% to about 5%, or an amount therebetween, of the culture medium having *Clostridium botulinum* from the growth phase is used to inoculate the fermentation medium. Fermentation is carried out to produce the maximum amount of microbial cells in a large-scale anaerobic environment (Ljungdahl et al., *Manual of industrial microbiology and biotechnology* (1986), edited by Demain et al, American Society for Microbiology, Washington, D.C. page. 84). Alternately, growth of *Clostridium botulinum* in the fermentation medium can proceed by adding the sample of the working cell bank directly to the fermentation medium.

In the prior art, growth of *Clostridium botulinum* in the culture medium typically proceeds in two stages, a first stage of cell plating, cell colony growth, selection and growth, followed by a second stage of inoculation of culture medium (typically a two stage step-up culture) and inoculation of fermentation medium and botulinum toxin production. Preferably, growth in the culture media in any stage does not result in cell lysis before inoculation of fermentation media with the final growth in culture medium. Thus, prior to our invention it took about four days to culture *Clostridium botulinum* bacteria before the fermentation step was begun. In accordance with our invention we are able complete all culturing in only 8 to 14 hours because there is no need for the previously utilized steps of plating cells, subsequent waiting time for colony growth on blood agar plates, selection of colonies from the plates for growth in small volumes of culture (e.g. 8-9 mL) that then provide an inoculum for the culturing medium. In accordance with one aspect of our invention, pre-selected cells are directly utilized to inoculate the culture medium that is then utilized to inoculate the full-scale fermentation medium from which botulinum toxin is eventually purified, thus eliminating the plating, colony formation, selection and step up steps previously utilized to grow cells that would inoculate a culture medium which is then itself utilized to inoculate fermentation medium.

Animal-based (non-APF or "NAPE") culture media generally include brain heart infusion media (BHI), bactopeptone, NaCl, and glucose. Culture media within the scope of our invention are APF culture media. For example, a soy-based product can be used instead of BHI and bactopeptone in the culture and fermentation media. Preferably, the soy-based product is soluble in water and comprises hydrolyzed soy, although *Clostridium botulinum* can grow in media containing insoluble soy. Any source of soy-based products may be used in accordance with the present invention. Preferably, the soy is hydrolyzed soy and the hydrolyzation has been carried out using non-animal enzymes. Sources of hydrolyzed or soluble soy include Hy-Soy (Quest International), Soy peptone (Gibco) Bac-soytone (Difco), AMISOY (Quest), NZ soy (Quest), NZ soy BL4, NZ soy BL7, SE50M (DMV International Nutritionals), and SE50MK (DMV).

EXAMPLES

The following examples set forth particular embodiments of our invention and are not intended to limit the scope of our invention. Unless otherwise set forth in the examples "toxin" or "botulinum toxin" means a botulinum toxin type A complex with a molecular weight of about 900 kDa. Systems and method disclosed herein for purifying a botulinum toxin type A complex with a molecular weight of about 900 kDa, have ready applicability to the purification of about 150 kDa, about 300 kDa, about 500 kDa as well as other molecular weight toxins, complexes, botulinum toxin serotypes and botulinum toxin neurotoxic component.

Example 1

Non-APF (Schantz) Process for Obtaining a Botulinum Toxin

This example sets forth the prior art Schantz process for obtaining botulinum neurotoxin. The process is a non-APF process using animal derived media and reagents (i.e. beef blood agar plates for culturing, casein in the fermentation medium and use of RNase and DNase enzymes for botulinum neurotoxin purification). FIG. 1A is a flow chart showing the major steps of the Schantz process. The Schantz process has about 16 to 20 major steps, for production scale work uses a 115 L fermentor and takes about 3 weeks to complete. The Schantz process is commenced by thawing a non-APF *Clostridium botulinum* master cell bank (MCB) vial to room temperature followed by four cultivation steps. First to select colonies with a suitable morphology, aliquots from the thawed MCB vial were streaked on pre-reduced Columbia blood agar (CBA) plates and anaerobically incubated for 30-48 hours at 34° C.±1° C. Second, selected colonies were inoculated into 9 mL test tubes containing a casein growth medium for 6-12 hours at 34° C. The contents of the 9 mL tube with the most rapid growth and highest density (growth selection step) were then further cultivated through two step-up anaerobic incubations (the third and fourth cultivation steps), being a 12-30 hour incubation at 34° C. in a 600 mL to 1 L seed cultivation bottle, followed by a cultivation in a 15 L to 25 L seed fermentor containing a casein growth medium for 6-16 hours at 35° C. These two step-up cultivations were carried out in a nutritive media containing 2% casein hydrolysate (a casein [milk protein] digest), 1% yeast extract and 1% glucose (dextrose) in water at pH 7.3.

The step-up cultivations were followed by a further incubation for 60-96 hours at 35° C. in a commercial scale (i.e. 115 L) production fermentor in a casein containing medium under a controlled anaerobic atmosphere. Growth of the bacterium is usually complete after 24 to 36 hours, and during the fermentation step carried out for about 65 to about 72 hours where most of the cells undergo lysis and release botulinum neurotoxin. It is believed that toxin is liberated by cell lysis and activated by proteases present in the media. A filtrate of the culture medium can be prepared using a single layer depth filter to remove gross impurities (i.e. whole and ruptured cells) thereby obtaining a clear solution referred to as a clarified culture. Collection of botulinum neurotoxin from clarified culture was accomplished by lowering the pH of the clarified culture to pH 3.5 with 3M sulfuric acid to precipitate the raw toxin at 20° C. (acidification precipitation). The raw botulinum neurotoxin was then concentrated (to achieve a volume reduction) by ultramicrofiltration (microfiltration) (referred to as MF or UF) followed by diafiltration (DF). A 0.1 μm filter was used for the microfiltration step.

The harvested crude or raw toxin was then transferred to a digestion vessel and stabilized by addition of the protease inhibitor benzamidine hydrochloride. DNase and RNase were added to digest (hydrolyze) nucleic acids. Hydrolyzed nucleic acids and low molecular weight impurities were then removed by further UF and DF steps. The toxin was then extracted with pH 6.0 phosphate buffer and cell debris removed by clarification. Next three sequential precipitation steps (cold ethanol, hydrochloric acid and ammonia sulfate precipitations) were carried out. The purified botulinum neurotoxin complex (bulk toxin) was stored as a suspension in a sodium phosphate/ammonium sulfate buffer at 2° C. to 8° C.

Completion of this Example 1 Schantz (non-APF) process, including the harvesting and purification steps, takes about two to three weeks. The resulting bulk botulinum neurotoxin was a high quality suspension of 900 kDa botulinum toxin type A complex made from the Hall A strain of *Clostridium botulinum* with a specific potency of $\geq 2 \times 10^7$ U/mg, an $A_{260}/A_{278}$ of less than 0.6 and a distinct pattern of banding on gel electrophoresis, and suitable for use for the compounding of a botulinum toxin pharmaceutical composition.

Botulinum neurotoxin can also be obtained from an APF, non-chromatographic process, as set forth in Example 7 of U.S. Pat. No. 7,452,697, the complete APF, non-chromatographic process (from beginning of culturing to end of all purification and processing steps) taking about two to three weeks to complete. Alternately, botulinum neurotoxin can also be obtained from an APF, chromatographic process, as set forth in Example 16 of U.S. Pat. No. 7,452,697, the APF, chromatographic process (from beginning of culturing to end of all purification and processing steps) taking a week or longer to complete.

Example 2

APF, Two and Three Column Chromatographic Systems and Processes for Obtaining a Botulinum Neurotoxin We developed rapid APF, anion-cation chromatographic based systems and processes for obtaining high yield, high purity botulinum neurotoxin. The process of this Example 2 had only 8-10 major steps, for production purposes (that is to obtain gram quantities of the final botulinum neurotoxin) used a 20 L fermentation vessel and takes only 4-7 days, preferably about 4 to about 6 days, to complete all step of the process from initiation of culturing to completion of final purification and toxin storage. Apparatus utilized in the systems herein disclosed are discussed below. Both a two chromatographic media process and a three chromatographic media process were developed and are set forth herein. The two media process used anion exchange chromatography followed by cation exchange chromatography. The three media process used anion exchange chromatography followed by cation exchange chromatography followed by hydrophobic interaction chromatography (HIC). The HIC removed further impurities such as a 49 kDa impurity (which turns out to be a host cell glucose phosphate isomerase, as discussed below).

Preparation of Working Cell Bank

We developed a new *Clostridium botulinum* cell bank (for use to initiate the culturing step) without use of Columbia blood agar plates, and which removed the need for colony selection prior to cultivation and also eliminated the need to carry out the Schantz process step up tube cultivation and multiple seed (cultivation) steps.

For this purpose, a previously established Schantz master cell bank (MCB) was used to create an APF research cell bank (RCB) from which a new APF master cell bank (MCB) and a subsequent working cell bank (WCB) were generated. A research cell bank (RCB) was made from a colony from the Schantz (NAPF) MCB. To remove the animal-derived protein from the MCB vial, the cells were washed twice in APF medium containing 2% w/v SPTII (Soy Peptone type II), 1% w/v yeast extract, and 1% w/v glucose. The cells were plated on APF medium under strict anaerobic conditions using a Modular Atmosphere Controlled System (MACS) anaerobic chamber. An isolated colony was further expanded and stored in APF medium containing about 20% glycerol below −135° C.

The APF-MCB was made under GMP conditions by expanding the RCB into oxygen-free APF medium (200 mL, reduced for a minimum of 12 hours in an anaerobic chamber) and cultured in a MACS anaerobic chamber at 34.5° C.±1° C. (stirred at 60 rpm) until the $OD_{540}$ of the culture reached 2.5±1.0 AU. Sterile glycerol was added to the resultant culture to a final concentration of about 20% after which the mixture was transferred into cryovials at 1 mL/vial (APF-MCB vials). The vials were flash frozen in liquid nitrogen, and then stored below −135° C. An APF-WCB was made under GMP conditions by expanding as above. The resultant APF cell banks were characterized for identity, purity, viability and genetic stability.

Upstream Steps (Culturing and Fermentation)

Our Example 2 process had two general stages; an upstream stage and a downstream stage. The upstream stage includes expansion of a starting cell line (growth and reproduction of *Clostridium botulinum* bacteria in a substantially APF culture medium), fermentation, harvest (removal of cellular debris) to provide a clarified, harvested culture that is then concentrated and diluted. Thus, in this example the nine steps of our two column process are culturing, fermentation, harvest filtration, concentration, capture (anion) chromatography, polishing (cation) chromatography, buffer exchange, bioburden reduction and vial fill.

The upstream stage included use of a culture medium in a 1 L bottle containing 400 mL of reduced (in an anaerobic chamber) seed APF culture medium (2% w/v SPTII, 1% w/v yeast extract, (adjusted to pH 7.3 with 1 N sodium hydroxide and/or 1 N hydrochloric acid prior to autoclaving)) 1% w/v sterile glucose added post autoclaving of culture media). The culture (seed) medium was inoculated with 400 μL of a thawed *Clostridium botulinum* WCB. Incubation/culturing occurred at 34.5° C.±1.0° C. with 150 rpm agitation in an anaerobic chamber.

When the optical density of the culture medium at 540 nm was 1.8±1.0 AU, the entire contents of the 1 L bottle (approximately 400 mL) were transferred to a 20 L production fermentor containing APF fermentation medium adjusted with 1 N sodium hydroxide and/or 1 N hydrochloric acid post-steam sterilization to pH 7.3, fermentation medium composed of 3.25% w/v SPTII, 1.2% w/v yeast extract, 1.5% w/v sterile glucose (added post sterilization; sterilization, e.g. at about 122° C. for 0.5 hour). The temperature and agitation were controlled at 35° C.±1° C. and 70 rpm, respectively. Nitrogen overlay was set at 12 slpm and headspace pressure set at 5 psig to maintain an anaerobic environment for cell growth. Fermentation pH and cell density were monitored by pH and online turbidity probes, respectively. The three phases for the production fermentation include exponential growth, stationary, and autolysis phases. Cellular autolysis, which releases active BoNT/A complex into the culture medium, was observed to occur consistently between 35 hours and the end of fermentation. At the end of fermentation, the culture was cooled to 25° C. for harvest.

Once the fermentation medium was cooled to 25° C., the cell debris was separated from the botulinum neurotoxin type A complex containing lysate by depth filtration, first through a 5-0.9 µm nominal retention rating gradient prefilter to remove cell debris, and then through a positively charged 0.8-0.2 µm nominal retention rating gradient to remove DNA (removal of up to about 80%). Both filters were rinsed together with 20 L of water for injection (WFI) before use. A minimum of 15 L of the filtrate was required for further processing, and any excess material was decontaminated after in-process sampling is complete. The filtrate was stored at 4° C. if not immediately processed by ultrafiltration.

Within a biosafety cabinet (BSC) the filtrate from the harvest step was concentrated from 15 L to 5±0.5 L using a hollow fiber, tangential flow filtration (TFF) membrane from GE Healthcare. The ultrafiltered material was then diluted with 10 mM sodium phosphate pH 6.5 buffer to a final volume of 20 L. This material was purified by use of either 2 column (anion then cation) or three chromatography columns (anion, cation, and then hydrophobic interaction). The diluted, ultrafiltered harvest material was stored at 4° C. if not immediately processed by purification.

In the Schantz process the culture step is ended and the fermentation step begun based on time and visual observation of culture growth. In contrast, in our Example 2 processes determination of when to end the culturing step is based on analysis of culture fluid optical density, which ensures that the culture is in the logarithmic growth phase at the time of commencement of the fermentation step, and permits reduction of duration of the culturing step to about 8 hours to about 14 hours. Our OD parameter terminated culture step maximized the health of the cultured cells and encouraged robust and abundant botulinum toxin resulting from the fermentation step. The average optical density (at 540 nm) of the culture medium at conclusion of culturing was 1.8 AU. The average duration of the fermentation step 72 hours and the average final turbidity ($A_{890}$) of the fermentation medium at conclusion of the fermentation step was 0.15 AU. The average amount of botulinum toxin type A complex present (as determined by ELISA) in the 20 L fermentation medium (whole broth) at the end of the fermentation step for was about 64 µg botulinum toxin type A complex/mL fermentation medium.

The harvest step used depth filtration to remove cell debris and nucleic acids, followed by ultrafiltration and dilution to prepare the fermentation medium for the next step in the process. This harvesting/cell debris clearing is fundamentally different from the Schantz harvest process, which uses precipitation by acidification followed by microfiltration and diafiltration to concentrate and exchange buffers in preparation for further processing.

Downstream Steps (Purification)

Downstream steps included capture of the botulinum neurotoxin on an anion exchange column, elution from the column and further separation from impurities by polishing on a cation exchange column, and preferably (in the three column process), passage of eluent containing desired botulinum neurotoxin through a third column, preferably a hydrophobic interaction column (e.g. chromatography), followed by concentration and buffer exchange using tangential flow filtration (TFF), and bioburden reduction (e.g. by further filtration using a 0.2 µm filter) to a final botulinum neurotoxin type A complex optimized for cold storage, preferably freezing, and eventual compounding into a botulinum neurotoxin type A complex pharmaceutical composition. The sequence of the chromatography and filtration stages was intended to remove product and process-related impurities, to remove potential adventitious agents and to control the botulinum neurotoxin type A complex concentration and buffer matrix of the final botulinum neurotoxin type A in order to provide a more stable drug substance.

A more detailed embodiment of the three column downstream process carried out is as follows. Clarified (diluted) ultrafiltered material (20 L, as disclosed above) was passed through a POROS® 50HQ anion exchange chromatography resin, the captured botulinum neurotoxin was eluted from the anion exchange column and then run through a POROS® 20HS cation exchange chromatography resin, the eluent from which was run through a Phenyl Sepharose HP chromatography resin. Eluent from the HIC column was subjected to 100 kDa tangential flow filtration, followed by 0.2 µm filtration. The resulting botulinum neurotoxin type A complex was frozen for storage.

In this Example, we used in the first chromatography step of the downstream process a POROS® 50HQ anion exchange chromatography resin packed into a column with an inner diameter of about 8 cm and a column height of about 15 cm. The entire POROS® 50HQ column operation was completed at ambient temperature, and the flow was in the downward direction. The botulinum neurotoxin type A complex was eluted from the anion column using a pH step change where the more negatively charged components such as nucleic acids (e.g. DNAs and RNAs) and other host cell proteins remained bound to the anion exchange column.

Particulars of the anion exchange step were: use of the POROS® 50HQ column using 0.1 N sodium hydroxide for a minimum contact time of 30 minutes (at least about 3 column volumes, at 230 cm/hour). The column was then equilibrated with a 50 mM sodium phosphate, pH 6.5 buffer (at least 5 column volumes). Next the clarified ultrafiltered and diluted material (i.e. processed lysate APF fermentation material) was loaded at 230 cm/hour onto the POROS® 50HQ anion exchange column, followed by washing with at least about 20 column volumes of 50 mM sodium phosphate, pH 6.5 at 230 cm/hour until absorbance at 280 nm of column effluent decreases to 0.10 AU, followed by eluting with 50 mM sodium acetate, pH 4.8 at 230 cm/hour. The product pool was collected, when the absorbance at 280 nm ($A_{280}$) increases to at least about 0.15 AU and through the peak maximum to equal or less than about 0.2 AU on the trailing edge, into a vessel containing 1 column volume of 50 mM sodium acetate, pH 4.8. This elution pool was stored at about 2° C. to about 8° C. for up to 48 hours.

The second chromatography step in the downstream process of this Example 2 used a POROS® 20HS cation exchange chromatography resin packed into a column with an inner diameter of 8 cm and a column height of 5 cm. The entire POROS® 20HS column operation was completed at ambient temperature, and the flow was in the downward direction. The botulinum neurotoxin type A complex associates with the POROS® 20HS column resin. The botulinum neurotoxin type A complex was then eluted from the column using a salt step change. The product-related impurities were eluted with the wash buffer and decontamination solution.

Particulars of the cation exchange step were: use of the POROS® 20HS column using 0.1 N sodium hydroxide solution for a minimum contact time of 30 minutes (at least about 3 column volumes, at 230 cm/hour). The column was then equilibrated with a 50 mM sodium acetate, pH 4.8 buffer (at least about 5 column volumes). Next the POROS® 50HQ product pool (collected as described above, fresh or from refrigeration) was loaded onto the POROS® 20HS column. The column was then washed with a 50 mM sodium acetate, pH 4.8 buffer (at least about 3 column volumes) and then washed again with a 50 mM sodium acetate, 150 mM sodium chloride, pH 4.8 buffer. The botulinum neurotoxin type A complex was eluted from the POROS® 20HS column with a 50 mM sodium acetate, 250 mM sodium chloride, pH 4.8 buffer at 200 mL/min, the eluate was diverted into a bioprocess collection bag (containing 1 column volume of 50 mM $NaH_3C_2O_2$, pH 4.8) when the $A_{280}$ increases to about ≥0.1 AU through peak maximum until the $A_{280}$ of the trailing edge of the elution peak decreases to a trailing edge value of ≤0.1 AU. The POROS® 20HS product pool was stored in the collection bag at ambient temperature for up to about 6 hours.

In the three-column chromatography media process of this Example 2, eluent from the second (cation exchange) column was passed through a HIC column. The HIC column used was a Phenyl Sepharose HP hydrophobic interaction chromatography resin packed into a column with an inner diameter of about 8 cm and a column height of about 5 cm. The entire Phenyl Sepharose HP column operation was completed at ambient temperature, and the flow was in the downward direction. The botulinum neurotoxin type A complex was eluted from the column using a decreasing salt step change. The impurities were eluted during the load and with the wash buffer and decontamination solution.

Particulars of the hydrophobic interaction chromatography step were: a Phenyl Sepharose HP column was initially sanitized with a 0.1 N sodium hydroxide solution for a minimum contact time of 30 minutes (with at least about 3 column volumes of a 0.1 N sodium hydroxide solution at 200 cm/hour). The column was then equilibrated with at least about 5 column volumes of 50 mM sodium acetate, 0.4 M ammonium sulfate, pH 4.8 buffer. Next the POROS® 20HS (cation exchange column) product pool (from above) was combined 1:1 with a 50 mM sodium acetate, 0.8 M ammonium sulfate, pH 4.8 buffer and loaded onto the Phenyl Sepharose HP column. The column was first washed with at least about 3 column volumes of a 50 mM sodium acetate, 0.4 M ammonium sulfate, pH 4.8 buffer, and then washed with a 50 mM sodium phosphate, 0.4 M ammonium sulfate, pH 6.5 buffer. Botulinum neurotoxin type A complex was eluted from the column with a 10 mM sodium phosphate, 0.14 M ammonium sulfate, pH 6.5 buffer. The eluate was diverted into a bioprocess collection bag when the $A_{280}$ increased to ≥0.05 AU. The eluate was collected until the $A_{280}$ of the trailing edge of the elution peak decreased to a value of ≤0.05 AU. The Phenyl Sepharose HP product pool was stored in the collection bag at ambient temperature for up to 6 hours.

A tangential flow filtration system was used to concentrate and diafilter the Phenyl Sepharose HP chromatography step product pool into the drug substance formulation buffer. Pall® Filtron Minimate cassettes with a 100 kDa molecular weight cut off membrane were used for the concentration and diafiltration steps. The formulated material was then passed through a Pall Mini Kleenpak® 0.2 μm filter to reduce the potential bioburden. As stated previously, the UF/DF step concentrated the Phenyl Sepharose HP product pool (eluent of the HIC column) to a BoNT/A complex concentration of 0.7 g/L and diafilters the concentrated material with a 10 mM potassium citrate, pH 6.5 buffer.

Particulars of the ultrafiltration/diafiltration process used were as follows. The UF/DF unit and Pall 100 kDa polyether sulfone membrane was initially flushed with a minimum of 5 L of water for injection (WFI) to remove the packing solution and sanitized with a minimum of 200 mL of a 1 N sodium hydroxide solution under recirculation conditions for a minimum of 10 minutes, preferably at least 30 minutes, to sanitize the UF/DF unit. Next the membrane and UF/DF system were equilibrated with sufficient volumes of the 10 mM potassium citrate, pH 6.5 formulation buffer until permeate and retentate pH was pH 6.5. After that the Phenyl Sepharose HP product pool was loaded onto the Minimate® tangential flow filtration cassette and the HIC eluate concentrated to 0.7 g/L. Following the concentration step, the retentate pool was diafiltered against a minimum of 5 diafiltration volumes of the drug substance formulation buffer (10 mM potassium citrate, pH 6.5) at a transmembrane pressure of 7.5 psig (pounds per square inch gauge). The permeate outlet was then closed and the UF/DF system run for at least 2 minutes and the system rinsed with 50 mL of 10 mM potassium citrate, pH 6.5 formulation buffer. After the rinse, the concentration of BoNT/A complex in the retentate pool was determined by measuring the offline $A_{278}$ and based on the $A_{278}$ reading, the concentration of the retentate pool was adjusted to 0.5 g/L with 10 mM potassium citrate, pH 6.5 buffer. The concentration-adjusted retentate pool was then filtered through a Pall Mini Kleenpak 0.2 μm filter to reduce potential bioburden. The filtered concentration-adjusted retentate pool was stored in a collection bag at 2° C.-8° C. for up to 2 days.

The final purified botulinum neurotoxin type A complex obtained was filled into 1 mL Nunc® cryovials at 700 μL per vial and stored frozen. The filling operation was carried out in a class 100 biosafety cabinet at ambient temperature.

The downstream process (including use of 2 or 3 chromatography columns) was completed in only 1 to 3 days and the botulinum neurotoxin type A complex obtained was stored frozen in a potassium citrate, pH 6.5 buffer at a concentration of 0.5 g/L as a solution. In comparison, the prior art Schantz downstream (toxin purification) process uses multiple filtration, precipitation, extraction and centrifugation steps to purify the botulinum neurotoxin type A complex and requires 1-2 weeks to complete just the downstream steps, and the resultant drug substance (recovered botulinum neurotoxin) is stored refrigerated as an ammonium sulfate suspension at a concentration of approximately 2.7 g/L. The use of chromatography instead of precipitation and the reduced processing time resulted in a significantly improved, consistent downstream process, as herein disclosed.

In accordance with one aspect, concentrations of vegetable-based products, such as soy-based products, can be Soy Peptone Type II Hy-Soy® or SE50MK(a Kosher soy peptone) in culture and fermentation media. Hy-Soy® in the seed culture medium can range between 10-200 g/L. Preferably, the concentration of Hy-Soy® in the seed medium ranges between 15-150 g/L. Most preferably, the concentration of Hy-Soy® in the seed medium is approximately between about 20-30 g/L or an amount therebetween. The concentration of glucose in seed medium can range between 0.1 g/L and 20 g/L. Preferably, the concentration of glucose ranges between 0.5-15 g/L. Most preferably, the concentration of glucose in the culture medium is approximately 10 g/L. Yeast extract amounts can be from about 5-20 g/L, more preferably from about 10-15 g/L or an amount therebetween. For example, the pH of the culture medium prior to growth of *Clostridium botulinum* can be approximately pH 7.0-7.5, or therebetween, preferably pH 7.3.

As an example, Hy-Soy® amounts in the production fermentation medium can range between 10-200 g/L. Preferably, the concentration of Hy-Soy® in the fermentation medium ranges between 15-150 g/L. Most preferably, the concentration of Hy-Soy® in the fermentation medium is approximately between about 20-40 g/L or an amount therebetween. The concentration of glucose in fermentation medium can range between 0.1 g/L and 20 g/L. Preferably, the concentration of glucose ranges between 0.5-15 g/L or an amount therebetween. Not necessarily, but as above, the glucose can be sterilized by autoclaving together with the other components of the fermentation medium. The pH level of the fermentation medium prior to growth can be pH 7.0-7.8, preferably about 7.0-7.5 or therebetween, more preferably pH 7.3.

As shown by the right hand side of FIG. 1, the two column APF process used in this Example 2 for obtaining a biologically active botulinum neurotoxin complex comprised the following steps: (a) culturing bacteria, such as *Clostridium botulinum* bacteria from an APF WCB vial, in a seed/culturing bottle, (b) then fermenting *Clostridium botulinum* bacteria in a fermentor (toxin production fermentor) having APF fermentation medium to expand the cell line, proceeding with fermentation and botulinum toxin production until a desired cell lysis phase is reached. Next, (c) harvesting (e.g. clarifying by filtration,) the APF fermentation medium to obtain a harvested fermentation medium, (d) proceeding with concentration and dilution resulting in a diluted harvested fermentation medium that is (e) passed through a capture column to remove impurities, (f) contacting eluent from the capture column with a polishing column to further remove impurities, and optionally a second polishing column (g) concentration and buffer exchange of the polishing column eluent, (h) followed by bioburden reduction filtration and the (i) filling of vials.

In one example, the fermentation volume is 20 L, the total process time for all steps was only 4 to 6 days, and high botulinum neurotoxin yield was obtained.

The following provides more details of a particular embodiment within the scope of our invention. The fermentation step was carried out in APF medium using a 30 L stainless steel fermentor.

In this example below, a much-reduced volume of fermentation medium was used while still providing a high yield of high potency botulinum neurotoxin type A complex. By using the following protocol, only 20 L or less, for example, of APF fermentation medium was required, instead of the typically larger, previous volumes (e.g. 115 L) of fermentation medium required for producing commercially useful amounts for obtaining a botulinum neurotoxin.

The MACS anaerobic workstation (Don Whitley) with airlock provided an oxygen-deficient environment in which to manipulate anaerobic organisms. Access to and egress from the chamber was via a porthole system, comprised of inner and outer doors. The unit was temperature controlled to maintain a user setting within the chamber. A humidistat-controlled condensing plate ensured the effective removal of excess moisture in the chamber. The chamber was illuminated for operator use and alarm for: low gas pressure, continuous gas flow, and loss of power conditions. The chamber was equipped with a HEPA filter to reduce viable and non viable particulate levels in the anaerobic chamber. Anaerobic conditions were maintained utilizing the "Anotox" and Palladium Deoxo "D" Catalyst atmospheric scrubbing system. Condensate water from the condensing plate was collected and piped to an external reservoir where it is removed.

As disclosed above, an APF process was used for preparation of an APF WCB, having cell bank vials stored below −135° C. An APF WCB cell bank vial was thawed at room temperature for about 15 min before culture medium inoculation, followed by a single cultivation step as disclosed above to establish a "seed" culture. This was carried out in a modular atmospheric controlled system utilizing aseptic techniques throughout, to minimize bioburden. The modular atmospheric controlled system was cleaned before undertaking inoculation of the completed seed culture vial with APF WCB vial contents. Culture medium was prepared using 1 N hydrochloric acid and 1 N sodium hydroxide (for pH adjustment), D(+) Glucose, Anhydrous (Mallinckrodt Baker, Cat#7730, 4.00 g), Soy Peptone Type II (SPTII) (Marcor, Cat #1130, 8.00 g), Water for Injection (WFI) 400.0 mL and Yeast Extract (YE) (BD Cat #212730, 4.00 g). The soy peptone Type II and yeast extract solution was made by measuring 300 mL of WFI with a 500 mL graduated cylinder and poured into a seed culture bottle. The seed culture bottle was placed onto a stirrer and the stirrer activated. 8.00 g of SPTII and 4.00 g of yeast extract was added to the seed culture bottle and mixed until dissolved. If dissolution was not complete after mixing, the mixture would be heated on low setting. The pH was measured and adjusted to about 7.30±0.05. The medium solution was brought up to about 360 mL with WFI. The seed culture bottle was adequately vented to allow steam and gas transfer. A 10% Glucose solution (w/v) was prepared by measuring about 30 mL of WFI with a 100 mL graduated cylinder and placed into the pre-assembled glucose addition bottle, which was placed onto a stirrer and the stirrer activated. About 4.00 g of glucose was added to the glucose addition bottle and mixed until dissolved (low heat was used if necessary to a dissolution) and qs (quantity sufficient) glucose solution to 40 mL with WFI. The glucose addition was then capped loosely with vent cap. Both the glucose and seed culture bottles are autoclaved at 123° C. for 30 minutes for sterilization. After sterilization, both items were removed from the autoclave and left to cool in a bio-safety cabinet. After cooling aseptically, 10% of the glucose solution was transferred into the seed culture bottle containing the yeast extract and soy peptone II solution and mixed, thereby providing a completed seed culture bottle.

This completed seed culture bottle was placed into the pre-cleaned MACS (wherein a prepared anaerobic indicator was placed). The cap of the completed seed culture bottle was loosened. The completed seed culture bottle was then placed on a stir plate within the MACS (stir plate activated to about 150 rpm) and the medium in the completed seed culture bottle was reduced for a minimum of 12 hours at about 34.5° C. +/−1° C. within the MACS, after which a 1 mL medium blank was sampled for optical density measurement (for biomass determination at 540 nm). Afterwards, the completed seed culture bottle, in the MACS (anaerobic) was inoculated. An APF WCB culture vial was obtained from the frozen cell bank and brought into the MACS. The vial was thawed for about 10-15 minutes, after which about 400 µL of the vial contents were placed directly into the medium in the completed seed culture bottle. The cap on the completed seed culture bottle was loosened completely and the cap was rested on top of the bottle and the stir pace was set to 150 rpm. After at least about 11 hours of incubation in the MACS, fermentation production was undertaken, as described below.

Probes (e.g. redox probe, pH probe, turbidity probe, e.g. by Broadley James and Optek) and sequence configuration of the fermentor, such as a 30 L stainless steel fermentor, were checked and calibrated, and inserted into their respective fermentor ports and tightened in place. For example, a fermentor can be a ABEC 30 L (VT) Fermentor System consisting of a 30 L volume fermentor vessel, an agitator drive system, piping assembly for utility connections (CIP, clean steam, CDA, Nitrogen, Oxygen, Process Chilled Water, bio-waste, and plant steam), instrumentation (pH, temperature, pressure, ReDox, optical density, and mass flow), and four peristaltic pumps. The bottom mounted agitator speed was controlled using an Allen-Bradley variable frequency drive (VFD). Semi-automatic and automatic control of the system is handled by an Allen-Bradley ControlLogix PLC with programming. The system was designed to provide closed-loop PID (proportional-integral-derivative) control of culture temperature, pressure, pH, and redox during fermentation operations. An Allen-Bradley DeviceNet® (an open device level network) is utilized for control and communication with devices and sensors on the skid.

For sterile hold, equilibrium, run and harvest modes, agitation, temperature, pressure and Nitrogen overlay are operated with the following set points.

For sterile hold and equilibrium mode:

| Controlled Parameter | Set Points and Range |
| --- | --- |
| Agitation | 100 rpm ± 10 |
| Nitrogen Overlay | 12 SLPM ± 2 |
| Fermentor Pressure | 5 psig ± 1 |
| Fermentor Temperature | 35 ± 1° C. |
| Redox | −390 to −150 mV |

For RUN mode:

| Controlled Parameter | Set Points and Range |
| --- | --- |
| Agitation | 70 rpm ± 5 |
| Nitrogen Overlay | 12 SLPM ± 2 |
| Fermentor Pressure | 5 psig ± 1 |
| Fermentor Temperature | 35 ± 1° C. |

For Harvest mode:

| Controlled Parameter | Set Points and Range |
| --- | --- |
| Agitation | 150 rpm ± 10 |
| Nitrogen Overlay | 10 SLPM ± 2 |
| Initial Fermentor Pressure | 0 psig |
| Fermentor Temperature | 25 ± 1° C. |

To prepare fermentation medium, material needed include D(+) Glucose, Anhydrous (Mallinckrodt Baker, Cat#7730, 300.0 g), Soy Peptone Type II (SPTII) (Marcor, Cat #1130, 650.0 g), Water for Injection (WFI, 13 L) and Yeast Extract (YE) (BD Cat #212730, 240.0 g), along with standard balances, a carboy (20 L, for example), glass bottle (5 L), graduated cylinders, stir bars and stirrers. About 10 L of WFI were added into the carboy along with a stir bar. The carboy was placed onto a stirrer and the stirrer was activated, after which about 650.0 g of soy peptone type II was added, along with about 240.00 g of YE. The fermentation medium was q.s. (quantity sufficient) to 13 L with WFI, and the carboy was capped. A 10% glucose solution (w/v) was then prepared by adding about 2 L if WFI into a glass 5 L bottle (with stir bar therein). Placed onto a stirrer and with the bar spinning, about 300.00 g of glucose was added into the bottle, and mixed until dissolved. The glucose solution was q.s. to 3 L with WFI and the bottled capped, thus providing a 10% glucose solution.

The fermentation medium in the carboy was added to the fermentor and pre-steam in place fermentor volume recorded and the fermentation sequence of operation was advanced. At the end of the SIP (steam in place) (122° C., +/−1° C.), the post-SIP fermentor volume was noted. A glucose addition assembly, comprising a vessel having tube therefrom with and in-line 0.2 µm filter (PALL Corp.) and peristaltic pump, was connected to the fermentor and the line was subjected to SIP and allowed to cool. An addition valve port was opened and about 3 L of glucose (filter sterilized) was added, and the appropriate amount of WFI (filter sterilized) to q.s. the total fermentor volume to 20 L was added to the glucose addition bottle and pumped into the fermentor through the same glucose filter line. The addition valve port was closed. The production fermentation medium had its pH adjusted thereafter, to about pH 7.3+/−0.05, with sterile 1 N sodium hydroxide or 1 N hydrochloric acid, utilizing SIP of addition lines, as required. Afterwards, parameters for sterile hold were set and held for about 12 hours before inoculation. The medium's starting glucose concentration was measured using a metabolite analyzer and glucose concentration recorded.

As stated above, at the end of seed culture incubation (about 11±1 hours), 1 mL of sample was taken for optical density (OD) measurement. OD was measured offline at 540 nm using a spectrophotometer and if within the appropriate range the OD value was recorded and culture was used for fermentation. The fermentor turbidity probe was accordingly zeroed. The seed inoculum bottle, from the anaerobic chamber, was brought over to the fermentor and a seed inoculum transfer assembly (a seed vessel with APF culture medium therein, the vessel having a culture inoculum transfer line with a sterile Kleenpak™ Connector assembly available from PALL Corp. or Millipore). The seed inoculum transfer line was then fixed to a peristaltic pump and the inoculum transfer line with sterile Kleenpak connector was connected to the fermentor. The fermentor pressure was lowered to 2 psig and entire volume of the seed inoculum bottle was pumped into the fermentor. At the end of inoculation, the online Absorbance Units (AU) from the fermentor was recorded, fermentor parameters were set to RUN mode and time was recorded.

Fermentation then proceeded (fermentation runs can be from about 60 hours to about 80 hours, preferably from about 68 hours to about 76 hours, most preferably for about 72 hours) while samples were taken from the fermentor, at 24 and 48 hours, for example, while maintaining aseptic conditions. Tests that were run on at least one sample taken during fermentation can include, but are not limited to, off-line optical density measurements, glucose measurements, ELISA, SDS-PAGE, Western blot, for example. At the end of the fermentation (end of fermentation broth volume is from about 18-19 L, for example), a sample may be taken (for testing by, for example, off-line optical density measurements, glucose measurements, ELISA, SDS-PAGE, western blot and DNA/RNA quantification.

At the end of the fermentation, online optical density, EFT (elapsed fermentation time), and fermentation end time was recorded, as well as agitation rpm, temperature in ° C., pressure psig and Nitrogen overlay slpm and redox mV. Next, the production fermentation broth was subjected to harvesting, i.e. the production fermentation broth is clarified through filtration whereby, for example, about 15 L of filtrate is collected. The fermentation parameters were set for HARVEST and the filter assembly for clarification was prepared (CUNO, 3M filtration) which includes a pre-filter, depth filter and at least one pressure gauge. The pre-filter and depth filter were flushed with about 20 L of water for injection. After flushing, the filtration assembly was attached to the harvest/drain port of the fermentor. The fermentor temperature was decreased to about 25° C., after which clarification of the fermentation broth begins (record clarification start time, initial online OD, initial pH, initial temperature and initial volume of fermentor). The pressure in the fermentor was increased at a rate of about 1 psi (pound per square inch) about every 10 minutes during filtration, until a pressure of about 6 psi was reached, at which the pressure was held until the end of harvesting. This filter removes approximately 80% of the RNA/DNA in the APF fermentation medium (the remainder essentially removed during later chromatography steps, as discussed below), thus doing away with prior reliance/use of RNase and/or DNase to remove such components from the fermentation broth. Process parameters, such as pre-filter inlet pressure, depth filter inlet pressure, fermentor pressure, agitation and filtrate volume were monitored at every 2 L of filtrate collected, at the end of which the clarification end time and volume of filtrate collected was recorded. Following completion of harvest step, the systems were decontaminated and cleaned.

The filtrate carboy was brought into the BSC for sampling, from which about 0 mL of filtrate was sampled for offline OD measurements and other analysis (e.g. ELISA, SDS-PAGE, DNA/RNA and western blot).

The filtrate was then subjected to ultrafiltration/dilution. A tangential flow filter (TFF) unit assembly was assembled. The TFF unit was rinsed for about 90 minutes with WFI at a preferred rate of about 2 L per minute and then the TFF unit was sanitized by running 0.1 N sodium hydroxide (re-circulated) therethrough for about 60 minutes, after which 1 L of 10 mM sodium phosphate buffer, pH 6.5 was run therethrough, followed by a rinse with WFI for about 30 minutes. The filtrate from the harvest step (about 15 L) was then passed through the TFF (this is carried out in a bio-safety cabinet), concentrating the filtrate down to about 5 L+/−0.5 L (the concentration step proceeds at about 2 L per minute and at a trans-membrane pressure of about 5 psig). A sample of the permeate can be taken and subjected to ELISA, dsDNA, SDS-PAGE and western blot tests, for example. Once concentrated to about 5 L+/−0.5 L, the retentate pool was then diluted up to about 20 L with about 15 L of sterile filtered 10 mM sodium phosphate buffer, pH 6.5, through the TFF, at about a rate of 2 L per minute. A sample can be then again be taken and subjected to ELISA, DNA/RNA, SDS-PAGE and western blot tests, for example. The ultrafiltration/dilution material (retentate) was stored at 4° C.

Following use all systems were decontaminated using either 1N sodium hydroxide or sterilization (steam) temperatures and cleaned.

The following materials, equipment and procedures were used to make the solutions, buffers, etc, set forth below for use in an exemplary process, that is in the purification of the fermentation medium obtained from the Example 2 processes so as to obtain a purified botulinum neurotoxin type A complex. Exemplary buffers utilized (filtered through a 0.2-micron vacuum filter and their conductivity measured in mS/cm, for recordkeeping) include: 10 mM sodium phosphate, pH 6.5; 50 mM sodium phosphate, pH 6.5; 50 mM sodium acetate, pH 4.8; 50 mM sodium acetate, 170 mM sodium chloride, pH 4.8; 50 mM sodium acetate, 250 mM sodium chloride, pH 4.8; 50 mM sodium acetate, 1 M sodium chloride, pH 4.8; 50 mM sodium acetate, pH 4.0 and 10 mM citrate, pH 6.5.

The following is an example of operations for purification and obtaining botulinum neurotoxin type A from the Example 2 processes. All product-contact parts were designed and constructed to ensure that they are non-reactive and non-absorptive. Additionally, all equipment was designed to allow the utilization of single use disposable systems or was designed and constructed to facilitate sanitization, cleaning and decontamination as per documented, validated methods. The systems or skids were designed to be non-product contacting while the flow paths are designed to be single use disposable, including the chromatography columns and the all associated tubing. Chromatography components were obtained from AlphaBio and UF/DF components were obtained from Scilog Inc. The chromatography set ups used included a peristaltic pump for solution delivery with variable speed drive, inlet valve manifold with 5 inlets, a column valve manifold with an array of 3 automated valves, outlet valve manifold with 3 outlets, column effluent monitoring, including pH, conductivity, and UV, peak collection based on UV absorbance, and instrumentation and controls required to complete the purification operations. The control system had both the software and hardware designed to control the purification process. Commands and data were entered via a HMI (Human Machine Interface) terminal. The operator initiated all automated process functions by commands at the HMI and monitored and adjusted process parameters such as feed flow rates, pressure, conductivity, pH, UV absorbance and individual valve positions.

The UF/DF system included of a recirculation pump, diafiltration pump, 2 balances and a tangential flow filter (TFF) holder. The recirculation pump interfaced with 3 disposable pressure sensors and one of the balances (located under the permeate reservoir) to control the flow rate to maintain a defined transmembrane pressure and stop, based on the weight of the permeate reservoir. The diafiltration pump interfaced with the second balance (located under the retentate reservoir) to start and stop, based on maintaining a constant weight of the retentate reservoir.

After concentration and dilution of retentate material from the harvesting step (harvesting the animal protein free fermentation medium), the material was loaded onto an anion exchange column. The following is the procedure used for packing and testing the anion exchange column useful in the Example 2 two column process.

Pre-packed columns were used for all three chromatographic steps. First, feed material (harvested APF media that had been subjected to ultrafiltration/dilution) was passed through the anion exchange column (Poros 50HQ, from ABI as described above). At least 5 column volumes (CVs) of 50 mM sodium phosphate, pH 6.5, were utilized to equilibrate the anion exchange column (in this example, a capture column).

After equilibration, the loading step was performed, where feed material (post harvesting step harvested fermentation broth, of about 20 L, for example)) was loaded onto the anion exchange column at a rate of about 200 cm/hr for example. After 0.5 column volume of loaded material had passed through the anion exchange column, the flow through (FT) pool was collected into a receptacle such as a polyethersulfone vessel, while toxin complex is bound to the anion exchange column material. This was followed by a wash step, where at least about 15 column volumes of the wash buffer (e.g. 50 mM sodium phosphate at a pH of 6.5) was passed through the anion exchange column. The wash step was stopped when the UV, measured at the column outlet, in real time, decreased to less than or equal to about 80 mAU. The wash buffer volume and the flow through/wash pool volume were recorded, and a 1 mL sample of the flow through/wash pool is taken and tested, for example, for toxin concentration, nucleic acid content, whole cell proteins, SDS-PAGE, qPCR, 2D LC and ELISA.

The next step was the elution step, where elution buffer (e.g. 50 mM sodium acetate, pH 4.8) was pumped onto the anion exchange column. When the UV reading at the column outlet, in real-time, increased to about 150 mAU or more, collection of eluate in a container pre-filled with 1 CV of elution buffer (50 mM sodium acetate, pH 4.8) was begun. Collection of eluate pool was stopped when the UV reading decreases to less than or equal to about 200 mAU (volume collected at this point is between about 1 to about 2 CVs). The chromatography system was then decontaminated and cleaned using 1 N sodium hydroxide.

The eluate pool from the anion exchange column was then prepared for addition onto the cation exchange column. The anion exchange eluate volume, pH, conductivity and feed temperature were recorded and the eluate pool from the anion exchange column was diluted with 1 CV of 50 mM sodium acetate, pH 4.8.

Following the run-through of the anion exchange column, cation exchange chromatography operation was undertaken. The cation exchange column (e.g. Poros® 20HS) was equilibrated with a minimum of 5 CVs of equilibration buffer (50 mM sodium acetate, pH 4.8). After equilibration, the diluted eluate pool from the anion exchange column was loaded onto the cation exchange column and the total volume loaded was recorded. After 0.5 column volume of loaded diluted eluate pool had passed through the cation exchange column, the flow through (FT) pool was collected. A first wash of the cation exchange column was conducted where about 3-5 CVs of 50 mM sodium acetate, pH 4.8, was passed through the cation exchange column (volume of first wash buffer utilized was recorded). A second wash was performed, where about 3 CVs of 170 mM sodium chloride, 50 mM sodium acetate, pH 4.8, was pumped through the column, this eluate being collected in a new container labeled "WASH 2 Peak". Collection was begun when the UV readings increase to greater than or equal to 50 mAU. 1 CV was collected and the second wash buffer volume utilized was recorded.

Elution of bulk toxin complex from the cation exchange column was carried out utilizing elution buffer (e.g. 250 mM sodium choride in 50 mM sodium acetate, pH 4.8) which was pumped onto the cation exchange column. When the UV reading of the elution reached at least about 100 mAU, eluate collection begun into containers pre-filled with dilution buffers (40 mL of 100 mM potassium phosphate, pH 6.8 and 60 mL of 10 mM potassium citrate, pH 6.5). Collection of eluate from the cation exchange column continued until UV readings decreased to about 100 mAU or less. The total volume of elute, after dilution, was recorded. The cation exchange chromatography system was then decontaminated and cleaned.

Following elution from the cation exchange column, the eluate was subjected to filtration. A tangential flow filtration (TFF) system was utilized, using three 100K MWCO membranes (Sartorius A G, Goettingen, Germany) stacked one atop the other. The cation exchange eluate pool initial volume was noted, as are the diafiltration/equilibration and sanitation solution descriptions. For example, the diafiltration solution can be 10 mM potassium citrate, pH 6.5 and the sanitation solution can be 0.1 N sodium hydroxide. System set up proceeded with connection of one tube from the reservoir containing either eluate from the cation column (IAPF) or HIC column (FAPF), the eluate containing botulinum toxin, through the ultrafiltration pump head into the inlet of the tangential flow filtration membrane. A second tube from the permeate outlet of the tangential flow filtration membrane was connected to the ultrafiltration (UF) permeate container. A tube from the retentate outlet of the tangential flow filtration membrane to the retentate reservoir was secured, and a fourth tube from the diafiltration (DF) buffer through the diafiltration pump head and into the retentate reservoir was also secured. The storage buffer of the system was flushed, as is the membrane, by flushing the membrane with at least about 720 mL of water for injection (WFI) with the retentate directed to waste, after which the membrane was further flushed with at least about 4200 mL of water for injection with the retentate recirculating to the reservoir. After this, membrane sanitation (if necessary) was carried out by flushing the membrane with at least about 200 mL of 1N sodium hydroxide with the retentate directed to waste, followed by a flushing of the membrane with at least about 200 mL of 1N NaOH with the retentate recirculating to the reservoir for a minimum of 30 minutes. Equilibration was then performed, by flushing the membrane with equilibration buffer (10 mM potassium citrate at a pH of 6.5), with retentate directed to waste until the retentate and permeate pH was within +/−0.2 units of the pH of the equilibration buffer (for example, within +/−0.2 units of pH 6.5).

The concentration of the material (eluate (product pool) from the cation exchange column) was determined, to see if dilution or concentration (exemplary processing) was appropriate (an example target concentration can be about 0.7 mg/mL). Dilution was accomplished utilizing 10 mM potassium citrate, pH 6.5. A target volume was determined, for example for a 0.7 mg/mL product concentration (target vol=(starting concentration/starting vol)/0.7 mg/mL).

The product pool (eluate (accordingly processed or not) from cation exchange column) was loaded onto the membrane and recirculation (with permeate outlet closed) of the system (TFF system) was run for at least 2 minutes with no backpressure, after which the permeate valve was slowly opened while adjusting the retentate back pressure valve to a target of about 7 psig transmembrane pressure. For dilution, 10 mM potassium citrate, pH 6.5 is added to target volume, and moved onto diafiltration without ultrafiltration; for concentration, ultrafiltration is begun. For diafiltration: permeate waste was collected in a new container (target diafiltration volume is 5× diafiltration volume) and diafiltered with at least 5 diafiltration volumes of 10 mM potassium citrate, pH 6.5. Diafiltration process data was collected at a minimum of 10-minute intervals (permeate weight g/vol mL, inlet pressure (psig), retentate pressure (psig), permeate pressure (psig) and transmembrane pressure (psig)). For recirculation/and rinse: with the permeate outlet filter closed, the system was recirculated/run for at least 2 minutes with no backpressure and the system was rinsed with at least 20 mL of 10 mM potassium citrate, pH 6.5. The product pool includes the retentate and the rinse. A sample can be taken from the product pool and subjected to verification analysis including, for example, UV at 278 nm, SDS-Page, LcHPLC, SE-HPLC, qPCR, RP-HPLC, Native-Page, AUC, Limulus amebocyte lysate, Western Blot and ELISA tests. For postuse cleaning, the system was flushed with 1N sodium hydroxide, recirculated for at least 10 minutes, after which the system was flushed and stored with 0.1 N sodium hydroxide therein.

Sterile filtration and filling was then conducted for storing and dividing the bulk neurotoxin. Concentration adjustment was performed to adjust toxin concentration, using 10 mM potassium citrate, pH 6.5, to about 0.5 mg/mL with the post rinse sample. If toxin concentration was less than about 0.5 mg/mL, then no concentration adjustment is needed.

Using a sterile pipette, 10 mL/0.75 mL aliquots into each of sterile 15 mL/1.5 mL sample tubes were made. The product container was gently stirred by hand and transfer the required amount of solution (containing bulk drug substance, i.e. bulk botulinum toxin) into each vial. The samples were stored a maximum of 5 days at 2° C.-8° C. refrigerator or 0.75 mL of the filtrate product pool was transferred to cryovials. The cryovials are stored at −70° C.+/−5° C.

Example 3

Compounding Method

A pharmaceutical composition suitable for administration to a patient can be made by compounding a botulinum neurotoxin obtained from an Example 2 process with one or more excipients. An excipient can act to stabilize the botulinum toxin during the compounding process and during a subsequent period of storage before use. An excipient can also function as a bulking agent and/or to provide a certain tonicity to the pharmaceutical composition. Compounding requires a many fold dilution of the botulinum neurotoxin obtained from an Example 2 process, mixing with one or more excipients (such as albumin [such as a human serum albumin or a recombinant human albumin] and sodium chloride) to thereby form a toxin composition, and preparation of a storage and shipment stable form of the toxin composition, as by lyophilizing, freeze drying or vacuum drying the composition. Thus, about 1.5 to 1.9 ng of the Example 2 obtained botulinum toxin type A complex is compounded with about 0.5 milligrams of recombinant human albumin (Delta Biotechnologies) and about 0.9 milligram of sodium chloride by mixing these three ingredients together followed by vacuum drying. Vacuum drying can take place from about 20° C. to about 25° C., at a pressure of about 80 mm Hg, for about 5 hours, at which time vials in which these components are vacuum dried are sealed under vacuum and capped, thereby obtaining a vial with about 100 units of botulinum neurotoxin type A complex. The resulting solid (powdered) vacuum dried product is, upon use, reconstituted with normal (0.9%) saline and used to treat patients with various indications, such as cervical dystonia and hyperhidrosis. Lyophilizing, vacuum or freeze drying prepares a storage and shipment stable form of the compounded botulinum neurotoxin.

In another example, from about 1.5-1.9 ng of the bulk botulinum toxin type A is compounded with about 0.5 milligrams of human serum albumin (Baxter/Immuno, Octapharma, and Pharmacia & Upjohn) and about 0.9 milligram of sodium chloride by mixing these three ingredients together followed by vacuum drying. Exemplary vacuum drying can take place from about 20° C. to about 25° C., at a pressure of about 80 mm Hg, for about 5 hours, at which time the vials in which these components are vacuum dried are sealed under vacuum and capped, thereby obtaining a vial with about 100 units of botulinum toxin. The resulting solid (powdered) vacuum dried product is, upon use, reconstituted with normal (0.9%) saline and used to treat patients with various indications, such as cervical dystonia and hyperhidrosis. Additionally, a pharmaceutical botulinum toxin composition can contain human serum albumin and/or lactose for example. In one example, about 1.5-1.9 ng of the bulk botulinum toxin type A can be compounded with about 125 micrograms of human serum albumin, and 2.5 milligrams of lactose and vacuum dried, lyophilized or freeze dried for storage stability, for example. In still another example, about 1.5-1.9 ng of botulinum neurotoxin obtained by the processes disclosed herein can be combined with about 10 mg of trehalose and about 0.5 mg of serum albumin (such as human serum albumin, native or recombinant), and optionally, about 1 milligram of methionine to provide about 100 units of botulinum toxin dried product. This composition can be lyophilized and be reconstituted later with, before use, about 1 mL of distilled sterile water or sterile unpreserved saline (0.9% sodium chloride for injection), for example. In particular examples, pharmaceutical botulinum toxin compositions can include sucrose, such as in an exemplary formulation having about 1.5-1.9 ng of botulinum neurotoxin obtained by the processes disclosed herein combined with human serum albumin 20% and sucrose, which can also be lyophilized to provide about 100 units of botulinum toxin type A, and later reconstituted with unpreserved saline (in a volume of about 0.5 mL to about 8.0 mL for example). In a particular example, 200 units of botulinum neurotoxin can be combined with about 10 mg of sucrose and 2 mg of human serum albumin per mL, and the resultant composition placed into vials and freeze-dried, to be later reconstituted before use with physiological saline.

Additionally, compounding can also utilize the neurotoxic component (i.e. the about 150 kDa component of the botulinum toxin type A complex, free of complexing proteins) of the botulinum toxin type A complex obtainable by the IAPF processes herein disclosed. In one method of purifying the about 150 kDa neurotoxic component from the associated non-toxic proteins (e.g. HAs, NTNH), type A neurotoxin is purified from the associated non-toxic proteins of the complex by a modification of the method of Tse et al. (1982) (Goodnough, M. C., 1994, Thesis, U W, Wis.). Botulinum neurotoxin complex obtained by our IAPF process (which utilizes either the 2-column anion-cation or 3-column anion-cation-HIC steps, as discussed above) is recovered from an DEAE-Sephadex A 50 (Sigma Chemical Co., St. Louis, Mo.), pH 5.5, column and is precipitated by addition of 39 g of solid ammonium sulfate/100 mL. The precipitated toxin complex is collected by centrifugation, dialyzed against 25 mM sodium phosphate, pH 7.9, and applied to a DEAE-Sephadex A50 column equilibrated with the same buffer. The neurotoxic component is separated from the non-toxic proteins of the complex and eluted from the column with a linear 0-0.5 M sodium chloride gradient. Partially purified neurotoxin component is recovered from the DEAE-Sephadex A50 column at pH 7.9 and dialyzed against 25 mM sodium phosphate, pH 7.0. The dialyzed toxin is applied to SP-Sephadex C50 (Sigma Chemical Co.) in 25 mM sodium phosphate, pH 7.0. Contaminating material does not bind to the column under these conditions. The pure neurotoxin (the about 150 kDa component) is eluted with a linear 0-0.25 M sodium chloride gradient. The about 150-kDa pure neurotoxin can be further purified by metal affinity chromatography, gel filtration or other methods of protein chromatography. As above, this pure neurotoxin (the about 150 kDa neurotoxic component of a botulinum toxin complex) can be lyophilized, vacuum or freeze-dried with the various excipients (e.g. serum albumin, sucrose, lactose, sodium chloride, trehalose, etc.) discussed above.

The bulk botulinum neurotoxin complex obtained by our IAPF process, can be compounded in numerous ways. Exemplary patents that disclose various formulations of botulinum toxins, such as U.S. Pat. No. 6,087,327 (discloses a composition of botulinum toxin types A and B formulated with gelatin); U.S. Pat. No. 5,512,547 (Johnson et al) entitled "Pharmaceutical Composition of Botulinum Neurotoxin and Method of Preparation" issued Apr. 30, 1996 and claims a pure botulinum type A formulation comprising albumin and trehalose, storage stable at 37° C.; U.S. Pat. No. 5,756,468 (Johnson et al) issued May 26, 1998 ("Pharmaceutical Compositions of Botulinum Toxin or Botulinum Neurotoxin and Method of Preparation"), and claims a lyophilized botulinum toxin formulation comprising a thioalkyl, albumin and trehalose which can be stored between 25° C. and 42° C.; U.S. Pat. No. 5,696,077 (Johnson et al) entitled "Pharmaceutical Composition Containing Botulinum B Complex" issued Dec. 9, 1997 and claims a freeze dried, sodium chloride-free botulinum type B complex formation comprising a type B complex and a protein excipient; and U.S. patent application publication number 2003/0118598 (Hunt) discloses uses of various excipients such as a recombinant albumin, collagen or a starch to stabilize a botulinum toxin (all of these published U.S. patent applications or U.S. patents are hereby incorporated by reference in their entirety), all provide examples of various useful formulations/excipients that may be used to compound the bulk botulinum neurotoxin provided by our IAPF process and provide a pharmaceutical composition.

The botulinum toxin complex obtained can be eluted from an ion exchange column in a pH 7-8 buffer to disassociate the non toxin complex proteins from the botulinum toxin molecule, thereby providing (depending upon the type of *Clostridium botulinum* bacterium fermented) botulinum toxin type A neurotoxic component with an approximately 150 kDa molecular weight, and a specific potency of $1\text{-}2\times 10^8$ $LD_{50}$ U/mg or greater; or purified botulinum toxin type B with an approximately 156 kDa molecular weight and a specific potency of $1\text{-}2\times 10^8$ $LD_{50}$ U/mg or greater, or purified botulinum toxin type F with an approximately 155 kDa molecular weight and a specific potency of $1\text{-}2\times 10^7$ $LD_{50}$ U/mg or greater.

Our invention provides many benefits. Firstly, the two and three column processes of Example 2 eliminates the use of animal source reagents and media (e.g. casein hydrolysate and Columbia blood agar plates) thus markedly decreasing the theoretical risks of patient exposure to prion-like agents or other infectious agents. Secondly, the two and three column chromatographic processes (and associated systems and apparatus) of example 2 are highly reproducible, as evidenced by excellent batch to batch consistency. This improvement translates to a more consistent clinical profile in patients who require repeated treatments with commercially available botulinum toxin containing compounds over several years. Analytical studies of drug substance (botulinum neurotoxin) from the herein disclosed IAPF processes (2 and 3 column) revealed a lower load of protein and nucleic acid impurities. This lower load of protein impurities translates into a lower risk of immunogenicity (antibody production). In addition, the improved purity of the IAPF process translates into a lower incidence of the non-specific symptoms commonly associated with biologic drugs (eg, nasopharyngitis, upper respiratory tract symptoms, musculoskeletal symptoms, headache, etc.). Furthermore, the improved downsized scale of this process decreases the risk of BoNT/A exposure in laboratory and manufacturing facility staff.

Exemplary advantages of the present invention include, for example:

1. Safety is improved since no component or substance derived from animal source (e.g. human or animal) is used in the process, use of DNase and RNase, Columbia blood agar plates, casein is eliminated (replaced, for example, by: charged filtration during the clarification/harvesting step and modern chromatography techniques; by seeding culture media directly with cells from a working cell bank, that is, cells previously selected and propagated/maintained in APF media; and culture bottle and fermentation media replaced with Soy Peptone Type II (SPTII) as a peptone source).

2. Between about 50 mg to about 200 mg of high quality botulinum toxin type A complex can be obtained per 10 L of fermentation medium.

3. The purified bulk toxin is obtained from a process which is robust, consistent, scalable, validatable, and cGMP compliant. Robust means the process is reproducible even upon an about ±10% change in one or more of the process parameters. Validatable means the process reproducibly provides consistent yields of purified toxin. cGMP compliance means that the process can be easily converted to a manufacturing process that complies with FDA required current Good Manufacturing Practices.

4. The potency of the final purified botulinum toxin complex meets or exceeds the potency (e.g. as determined by the MLD50 assay) of purified botulinum toxin complex obtained from a Schantz or modified Schantz process.

5. Replacement of any precipitation steps with chromatographic steps to purify a bulk botulinum toxin complex, which improves the specificity of the purification process.

6. New improved process facilitates reduction of scale resulting in improved handling and achievement of an operational success rate of >95% (for example, reduced from typical volumes utilizing 110 L-120 L of fermentation media down to about 10 L to about 50 L, even down to about 2 L to about 30 L of fermentation media or an amount therebetween. Typical current production scale for bulk drug substance is 115 L of non-APF fermentation medium, and has, as one aspect of our invention, been reduced to 20 L of fermentation medium. This reduction in scale is made possible by optimizing the synthesis and cellular release of the BoNT/A complex as well as overall yield across the purification steps, resulting in similar quantity of final bulk botulinum toxin (drug substance) as obtained in prior processes requiring, for example 5× or even more fermentation volumes (e.g. 115 L). This reduced scale facilitates easier management of the fermentation working volume and thus minimizes the potential risk of operator exposure to the BoNT/A complex, an important operational and safety advantage.

7. Due to the potentially lethal nature of the BoNT/A complex, closed systems have been implemented throughout the manufacturing process as herein disclosed. Unlike prior art methods, no drug substance material produced in accordance with aspects of the present invention is exposed to the environment during transfer between unit operations; all operations are wholly contained.

8. The bulk botulinum toxin manufacturing process herein disclosed is simplified at all steps without sacrificing the identity, quality, purity, or potency of the drug substance during manufacture. A number of steps utilized in a non- APF process have been eliminated in the redesigned IAPF process, thereby reducing production time from, for example, 21 days to 6 days or less.

9. The storage condition of bulk botulinum toxin as a frozen solution greatly improves drug substance stability.

Various publications, patents and/or references have been cited herein, the contents of which, in their entireties, are incorporated herein by reference. Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. Moreover, any combination of the above-described elements in all possible variations thereof is encompassed by the invention unless otherwise indicated herein or otherwise clearly contradicted by context.

Although the present invention has been described in detail with regard to certain preferred methods, other embodiments, versions, and modifications within the scope of the present invention are possible. Accordingly, the spirit and scope of the following claims should not be limited to particular descriptions of the embodiments set forth above.

We claim:

1. A process for producing a biologically active botulinum neurotoxin, the method comprising the following steps:
   (a) providing a fermentation medium which is free of animal-derived products;
   (b) fermenting *Clostridium botulinum* bacteria in the fermentation medium;
   (c) contacting the fermentation medium with an anion exchange chromatography medium;
   (d) contacting an eluate of the anion exchange chromatography medium with a cation exchange chromatography medium; and
   (e) eluting an eluate containing botulinum neurotoxin from the cation exchange chromatography medium;
   wherein no animal-derived enzyme is used to purify the botulinum neurotoxin.

2. A process according to claim 1, further comprising the step (f) of contacting the eluate of step (e) with a hydrophobic interaction chromatography medium and eluting an eluate containing botulinum neurotoxin.

3. A process according to claim 1, wherein the obtained botulinum toxin comprises no more than one part residual nucleic acid per million parts of the botulinum toxin.

* * * * *